(12) United States Patent
Bachinski et al.

(10) Patent No.: US 8,768,473 B2
(45) Date of Patent: Jul. 1, 2014

(54) SYSTEMS AND METHODS FOR THERAPEUTIC ELECTRICAL STIMULATION

(71) Applicant: Empi Inc., Vista, CA (US)

(72) Inventors: Thomas Jerome Bachinski, Lakeville, MN (US); Richard Paul Shindley, Big Lake, MN (US); Dennis Lutz, Lino Lakes, MN (US)

(73) Assignee: EMPI Inc., Vista, CA (US)

( * ) Notice: Subject to any disclaimer, the term of this patent is extended or adjusted under 35 U.S.C. 154(b) by 0 days.

(21) Appl. No.: 13/868,587

(22) Filed: Apr. 23, 2013

(65) Prior Publication Data

US 2013/0238075 A1    Sep. 12, 2013

Related U.S. Application Data

(63) Continuation of application No. 12/319,539, filed on Jan. 7, 2009, now Pat. No. 8,452,409, which is a continuation-in-part of application No. 12/276,068, filed on Nov. 21, 2008, now Pat. No. 8,386,032.

(60) Provisional application No. 61/019,489, filed on Jan. 7, 2008.

(51) Int. Cl.
*A61N 1/00* (2006.01)
*A61B 5/04* (2006.01)

(52) U.S. Cl.
USPC ............... 607/46; 607/2; 607/115; 607/117; 600/388

(58) Field of Classification Search
USPC .................. 607/2, 46, 115, 117; 600/388
See application file for complete search history.

(56) References Cited

U.S. PATENT DOCUMENTS

| | | | |
|---|---|---|---|
| 1,428,358 | A | 9/1922 | Burbery |
| 3,895,635 | A | 7/1975 | Justus et al. |
| 4,040,697 | A | 8/1977 | Ramsay et al. |
| 4,178,052 | A | 12/1979 | Ekbom et al. |
| 4,253,721 | A | 3/1981 | Kaufman |
| 4,268,101 | A | 5/1981 | Stone |
| 4,390,223 | A | 6/1983 | Zenkich |
| 4,671,591 | A | 6/1987 | Archer |
| 4,690,144 | A | 9/1987 | Rise et al. |
| 5,277,613 | A | 1/1994 | Neward |

(Continued)

FOREIGN PATENT DOCUMENTS

| | | | |
|---|---|---|---|
| FR | 964611 | A | 5/1950 |
| GB | 257145 | A | 8/1926 |

(Continued)

OTHER PUBLICATIONS

Extended European Search Report dated Dec. 14, 2010 in European Patent Application No. 09700152.3-2305 / 2237831.

(Continued)

*Primary Examiner* — Nicole F Lavert
(74) *Attorney, Agent, or Firm* — Knobbe, Martens, Olson & Bear, LLP.

(57) ABSTRACT

In various embodiments, the invention disclosed herein provides systems, devices and methods for providing electrical stimulation to a patient. An electrical mechanical interconnection is provided to facilitate user friendly systems and devices. Exemplary therapeutic electrical stimulation devices include a shoe connected mechanically and electrically to a conductor that provides signals for electrical stimulation.

25 Claims, 30 Drawing Sheets

(56) References Cited

U.S. PATENT DOCUMENTS

| | | | |
|---|---|---|---|
| 5,326,272 | A | 7/1994 | Harhen et al. |
| 5,466,017 | A | 11/1995 | Szabo et al. |
| 5,498,235 | A | 3/1996 | Flower |
| 5,562,607 | A | 10/1996 | Gyory |
| 5,562,707 | A * | 10/1996 | Prochazka et al. ............ 607/2 |
| 5,895,298 | A | 4/1999 | Faupel et al. |
| 5,895,369 | A | 4/1999 | Flower |
| 6,142,949 | A | 11/2000 | Ubby |
| 6,445,955 | B1 * | 9/2002 | Michelson et al. .......... 607/46 |
| 6,687,536 | B1 | 2/2004 | Beck et al. |
| 7,066,767 | B2 | 6/2006 | Liao |
| 7,214,107 | B2 | 5/2007 | Powell et al. |
| 7,255,609 | B1 | 8/2007 | Epstein |
| 7,270,580 | B2 | 9/2007 | Bradley et al. |
| 7,364,440 | B2 | 4/2008 | Gobron et al. |
| 7,574,262 | B2 | 8/2009 | Haugland et al. |
| 2004/0039275 | A1 | 2/2004 | Sato et al. |
| 2004/0072475 | A1 | 4/2004 | Istvan |
| 2004/0106964 | A1 | 6/2004 | Fischer et al. |
| 2005/0107841 | A1 * | 5/2005 | Meadows et al. ............ 607/43 |
| 2005/0131506 | A1 * | 6/2005 | Rezai et al. .................. 607/117 |
| 2005/0181341 | A1 | 8/2005 | Ewing et al. |
| 2006/0195152 | A1 | 8/2006 | Gerber |
| 2007/0088419 | A1 | 4/2007 | Fiorina et al. |
| 2007/0191912 | A1 | 8/2007 | Fischer et al. |
| 2008/0254684 | A1 | 10/2008 | Tracy et al. |
| 2009/0149731 | A1 | 6/2009 | Selvitelli et al. |
| 2009/0182394 | A1 | 7/2009 | Bachinski |

FOREIGN PATENT DOCUMENTS

| | | |
|---|---|---|
| WO | WO-0103768 A1 | 1/2001 |
| WO | WO-2006113801 A2 | 10/2006 |
| WO | WO-2009/148595 A2 | 12/2009 |

OTHER PUBLICATIONS

International Search Report and Written Opinion dated Dec. 20, 2011 in International Application No. PCT/US2011/047398.

International Search Report and Written Opinion in International Application No. PCT/US2009/000082.

Notice of Allowance in U.S. Appl. No. 12/856,382 dated Feb. 6, 2012.

Notice of Allowance in U.S. Appl. No. 12/319,539 dated Jan. 29, 2013.

Notice of Allowance received in U.S. Appl. No. 12/276,068 dated Oct. 17, 2012.

Non-Final Office Action received in U.S. Appl. No. 13/464,208 dated Nov. 16, 2012.

* cited by examiner

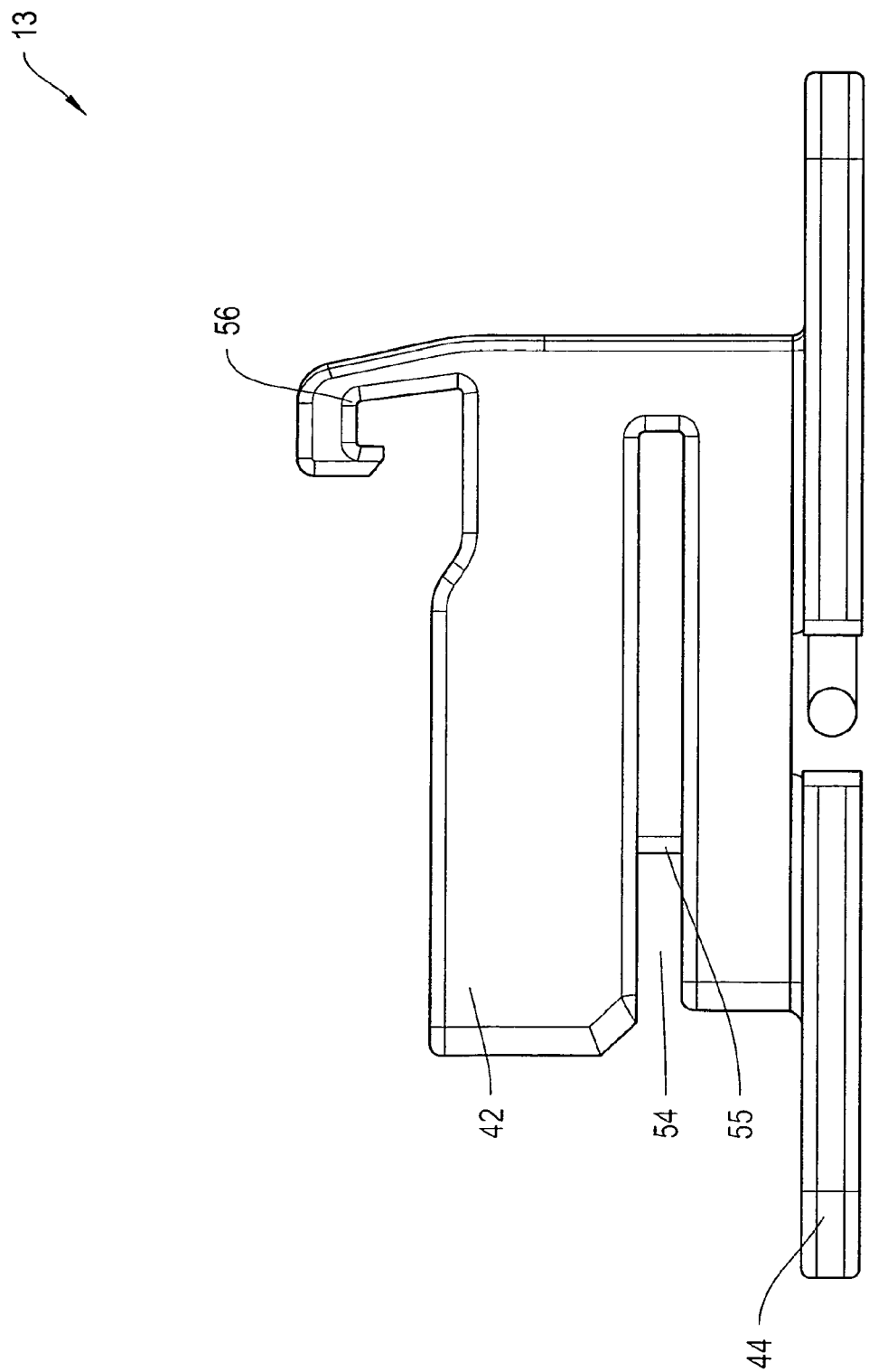

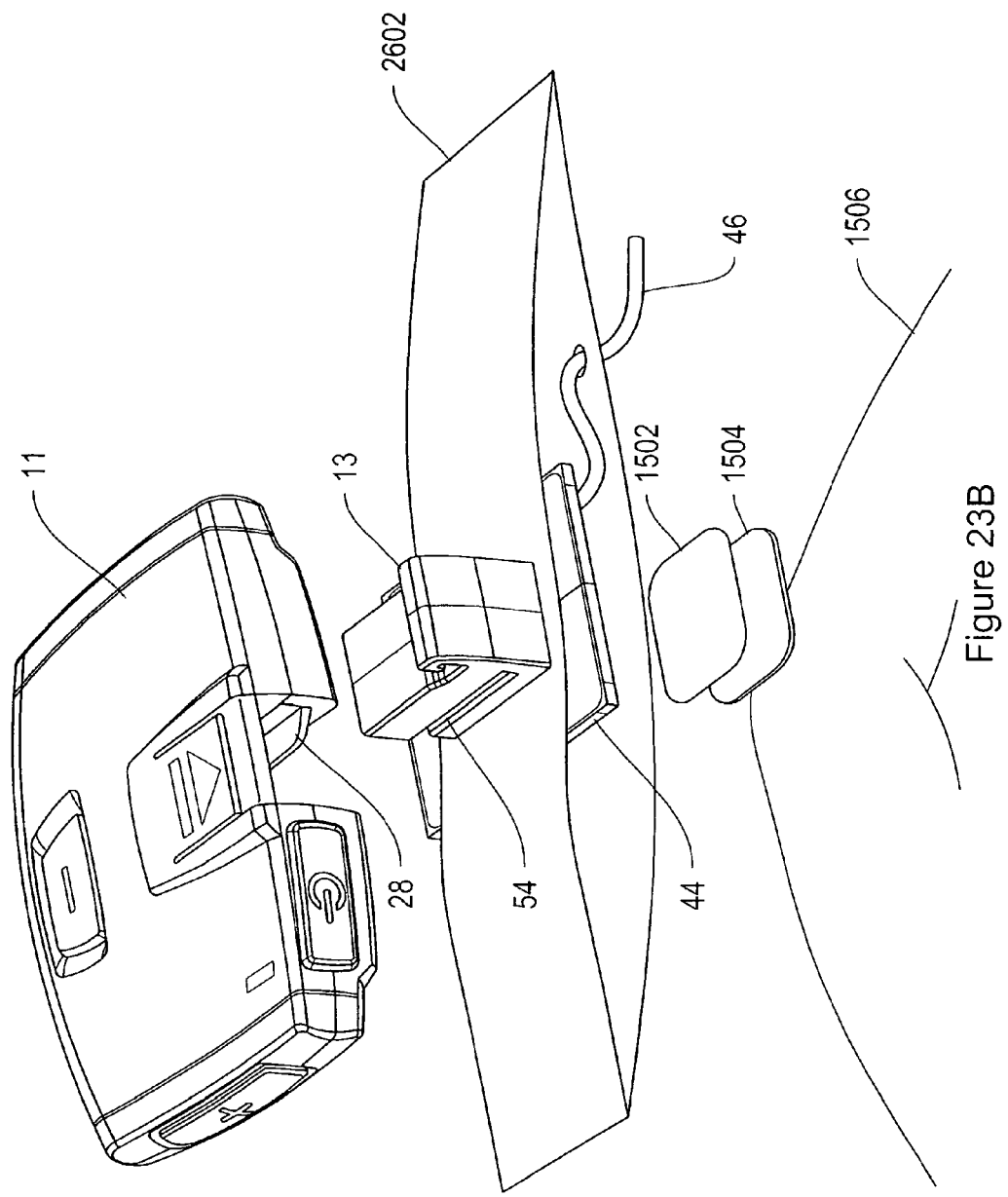

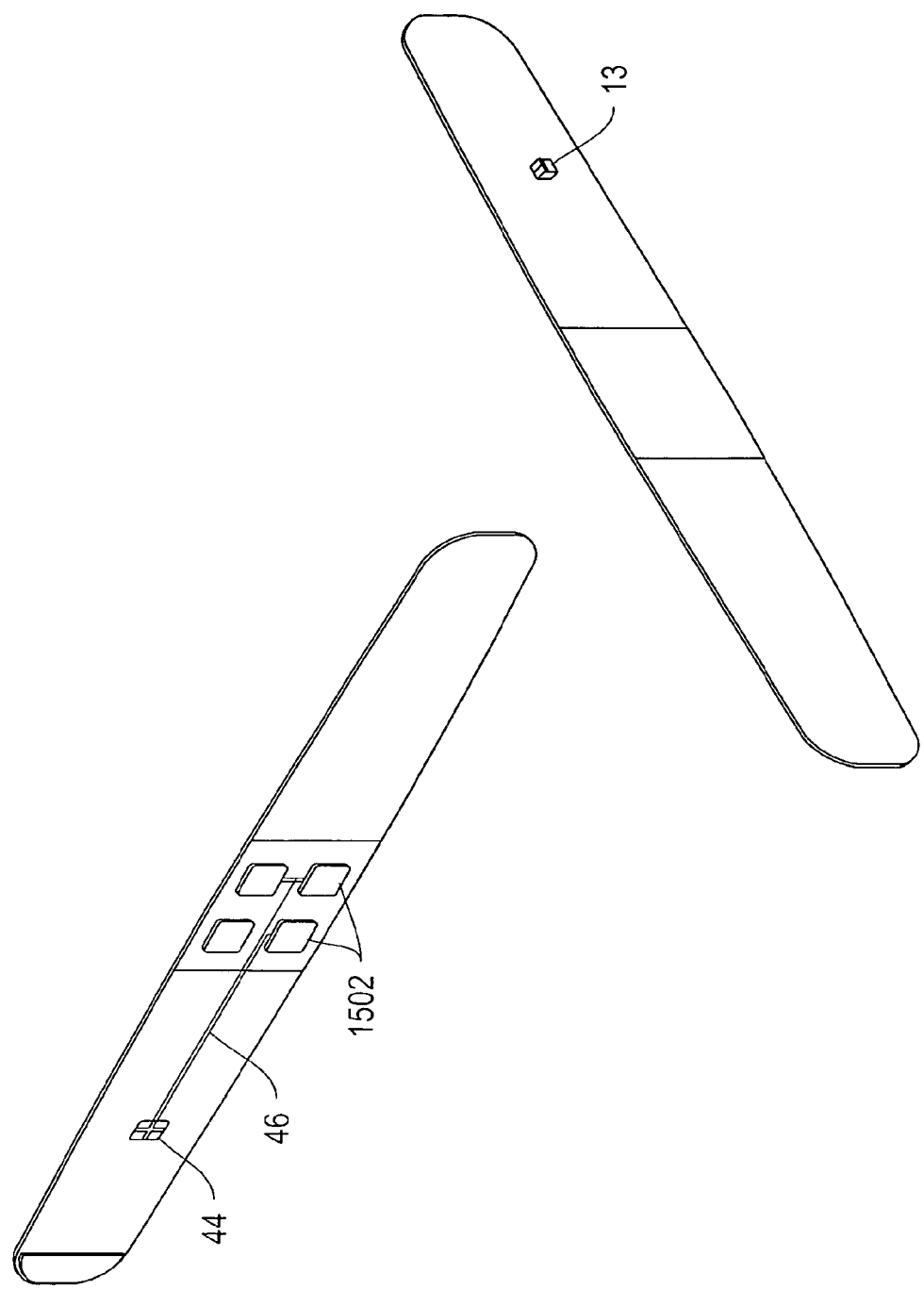

SYSTEMS AND METHODS FOR THERAPEUTIC ELECTRICAL STIMULATION

RELATED APPLICATIONS

This application is a continuation of U.S. application Ser. No. 12/319,539 filed Jan. 7, 2009, now U.S. Pat. No. 8,452,409, which is a continuation-in-part of U.S. application Ser. No. 12/276,068 filed Nov. 21, 2008, now U.S. Pat. No. 8,386,032 and which claims the benefit of U.S. Provisional Application No. 61/019,489 filed Jan. 7, 2008, now expired, all of which are incorporated by reference herein in their entirety.

BACKGROUND

Low-power electrical stimulation has been found to have various therapeutic uses. One example of low-power electrical stimulation is transcutaneous electrical nerve stimulation ("TENS"). TENS devices typically operate by generating low-power electrical impulses that are supplied to the skin of a patient through electrodes. The electrical impulses have been found to diminish or completely relieve pain previously felt by a patient.

There are two primary theories for the effectiveness of TENS devices. The first theory is the Gate Control Theory. In this theory, the mild electrical stimulation is thought to relieve pain in a similar way as when an injured area is manually rubbed. Rubbing acts to mask the pain from the injury. Similarly, when electrical impulses pass through the skin they pass through portions of the peripheral nervous system. The electrical impulses reduce the transmission of pain messages, thereby diminishing or completely relieving pain.

A second theory is the Endorphin Release Theory. This theory states that the electrical impulses from the TENS device cause mild to moderate muscle twitching in the body. The body responds to the muscle twitching by producing natural pain relievers called endorphins, thereby diminishing or completely relieving the pain.

In addition to TENS, electrical stimulation has also been found to be useful for other therapies. Examples include edema reduction, wound healing, iontophoresis drug delivery, muscle stimulation, and interferential current therapy.

Currently available TENS devices are subject to several drawbacks that impair their usability for a patient. For example, some devices are bulky and have many wires that get tangled or in the way of the user. The wiring and bulky housings of some current TENS devices can also be obtrusive and embarrassing for a user to wear in public. In addition, many devices are complex and lack a simple, user-friendly connection mechanism between controller and electrodes to allow a user to easily connect or disconnect the device. The drawbacks of current TENS devices prevent a user from seamlessly integrating electrical stimulation therapy into their everyday lives.

SUMMARY

In general terms, this disclosure is directed to therapeutic electrical stimulation and addresses various shortcomings with currently available electrical stimulation technologies. In one aspect, the systems, devices and methods disclosed herein provide improved usability of electrical stimulation devices. Certain embodiments of the present disclosure provide a therapeutic electrical stimulation device that is user friendly and easy to wear, comprising a controller for providing electrical signals for electrical stimulation of the patient and an electro mechanical intermediate connector arranged to convey the electrical signals from the controller to the patient. The controller includes a power source, an electrical signal generator, and a receptacle, wherein the electrical signal generator is electrically coupled to the power source, and wherein the electrical signal generator generates electrical signals that are provided to a conductor associated with the receptacle. In certain embodiments, the electro mechanical connector is an interconnecting patch. An exemplary patch includes a shoe, an insulating layer, and electrodes, wherein the shoe is removably mechanically connected to the controller at the receptacle, the shoe is electrically coupled to the conductor at the receptacle, and the electrodes are electrically coupled to the shoe.

Another aspect is a more user friendly controller for a therapeutic electrical stimulation device, the controller comprising a power source including a rechargeable battery; an electrical signal generator powered by the power source and generating an electrical signal, and a receptacle including at least one conductor. The conductor is electrically coupled to the electrical signal generator to receive the electrical signal. The receptacle is arranged and configured to receive a portion of an electro mechanical interconnecting patch to electrically couple a portion of the patch with the conductor.

Yet another aspect is a patch for a therapeutic electrical stimulation device, the patch comprising an insulating layer having a first side and a second side; a shoe connected to the first side of the patch and including at least two conductors, wherein the shoe is configured for insertion into a receptacle of a controller of the therapeutic electrical stimulation device; at least two electrodes adjacent the second side of the patch, wherein each conductor is electrically coupled to one of the electrodes; and an adhesive layer connected to the second side of the insulating layer.

A further aspect is a method of connecting a patch with a controller of a therapeutic electrical stimulation device, the method comprising advancing the controller in a first direction toward that patch to insert a shoe of the patch into a receptacle of the controller; and advancing the controller in a second direction to cause the controller to engage with the shoe.

Another aspect is a method of adjusting the operation of a therapeutic electrical stimulation device, the method comprising operating the therapeutic electrical stimulation device in a first mode by executing a first firmware algorithm; downloading a second firmware algorithm; installing the second firmware algorithm onto the therapeutic electrical stimulation device; and executing the second firmware algorithm to operate the therapeutic electrical stimulation device in a second mode.

A further aspect is a docking station comprising a housing; a slot in the housing arranged and configured to receive a therapeutic electrical stimulation device; a power source for supplying power to a therapeutic electrical stimulation device to recharge a battery; and a data communication device for communicating between the therapeutic electrical stimulation device and a communication network.

In one aspect a system is provided for delivering therapeutic electrical stimulation. The system includes a patient interface component, a controller component that provides signals for electrical stimulation, and an intermediate electro-mechanical connection component positioned between the patient interface component and the controller component. The intermediate component matingly engages with the controller component and includes conducting lines that interface with leads in the controller component to provide electrical communication between the patient interface and the controller component. Each component has a useful life that is determined either by the device supplier, government regulation, or by natural wear and tear of the component itself. In certain embodiments, the useful life of the component is predetermined prior to initial use or sale of the component, and it is replaced upon expiration of the useful life. In some implementations, the predetermined useful life coincides with a period established by regulatory or other administrative authority by paying for or reimbursing for such component. In some embodiments, such predetermined useful life is shorter than the period in which the component becomes physically worn out or inoperable.

In certain embodiments, the patient interface component has a useful life that is shorter than the useful life of the intermediate component, and the intermediate component has a useful life that is shorter than that of the controller component. In certain embodiments, the controller component has a useful life of about five years, the intermediate component is a multiuse component having a useful life of about six months or less, and the interface component is a single use disposable.

In one aspect, the system provides an electro-mechanical interface between the patient and an electro stimulation source. In certain embodiments, the interface has disposable and reusable component. In certain implementations, the electromechanical interface is formed from at least two disposable components, with each having a useful life of different length than that of the other. In some embodiments, the system provides a disposable patient contact layer, a disposable/reusable intermediate module, and a reusable controller.

A further aspect is a garment that carries the components and is adapted to position the patient interface component against the patient.

Yet another aspect is a controller component that has a receptacle with a least one conductor, the conductor is electrically coupled to an electrical signal generator to receive the electrical signal. The receptacle is configured to receive a portion of the intermediate component to electrically couple a portion of the intermediate component with the conductor.

In another aspect, the intermediate component is a patch, the patch comprising a shoe connected to at least one insulating layer and including at least one conductor, wherein the shoe is configured for insertion into the receptacle of the controller component.

This summary is provided to introduce a selection of concepts in a simplified form that are further described below in the Detailed Description. This Summary is not intended to identify key or essential features of the claimed subject matter, nor is it intended to be used in any way as to limit the scope of the claimed subject matter.

DESCRIPTION OF THE DRAWINGS

FIG. 7 is a side plan view of a shoe of the therapeutic electrical stimulation device shown in FIG. 1.

FIG. 23B is an exploded perspective view of an exemplary implementation of the devices shown in FIG. 23A.

FIG. 23D is a perspective view of a possible configuration for the devices shown in FIG. 23A.

DETAILED DESCRIPTION

Figure 1:
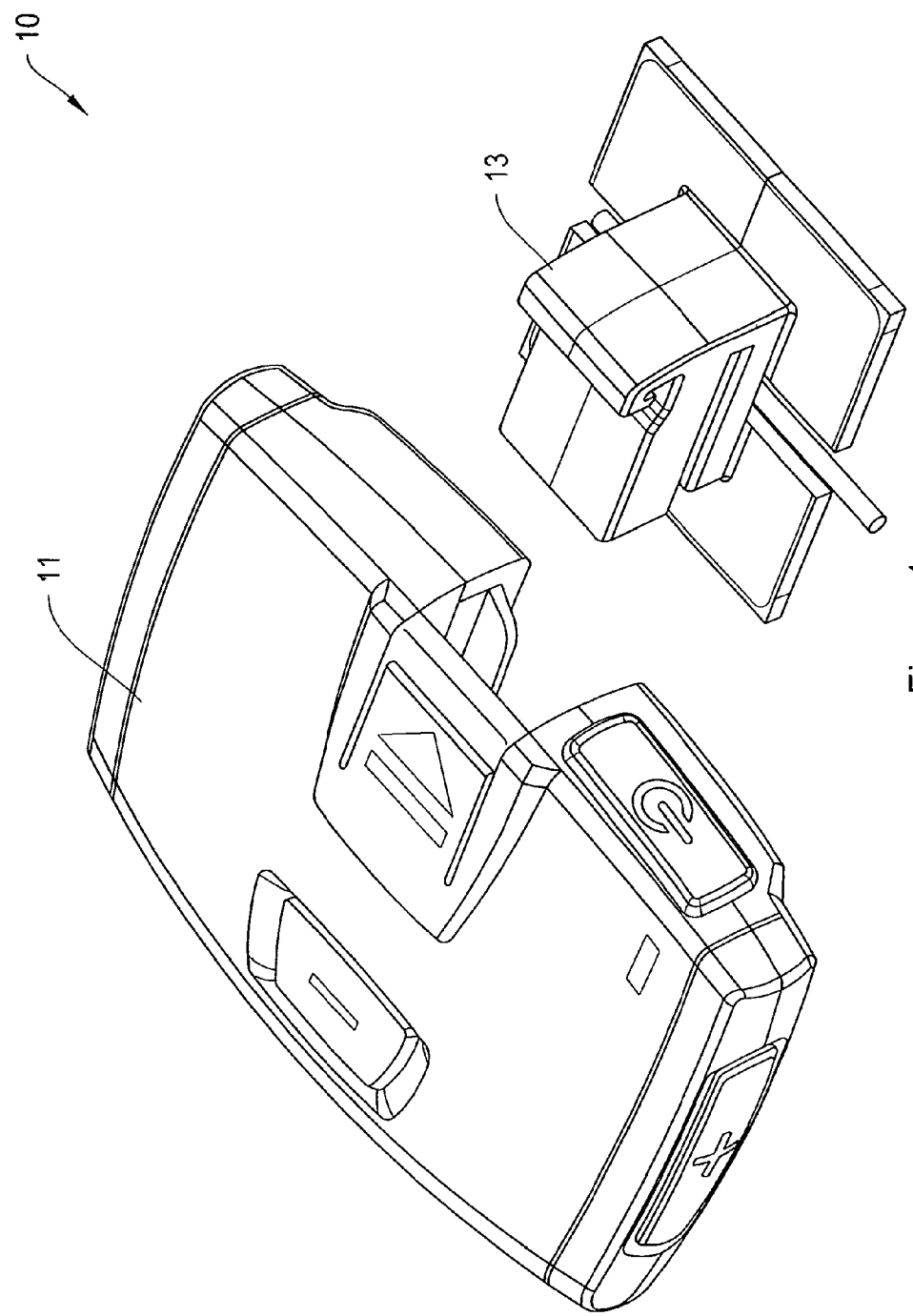
FIG. 1 is a perspective top view of an example therapeutic electrical stimulation device.
Figure 2:
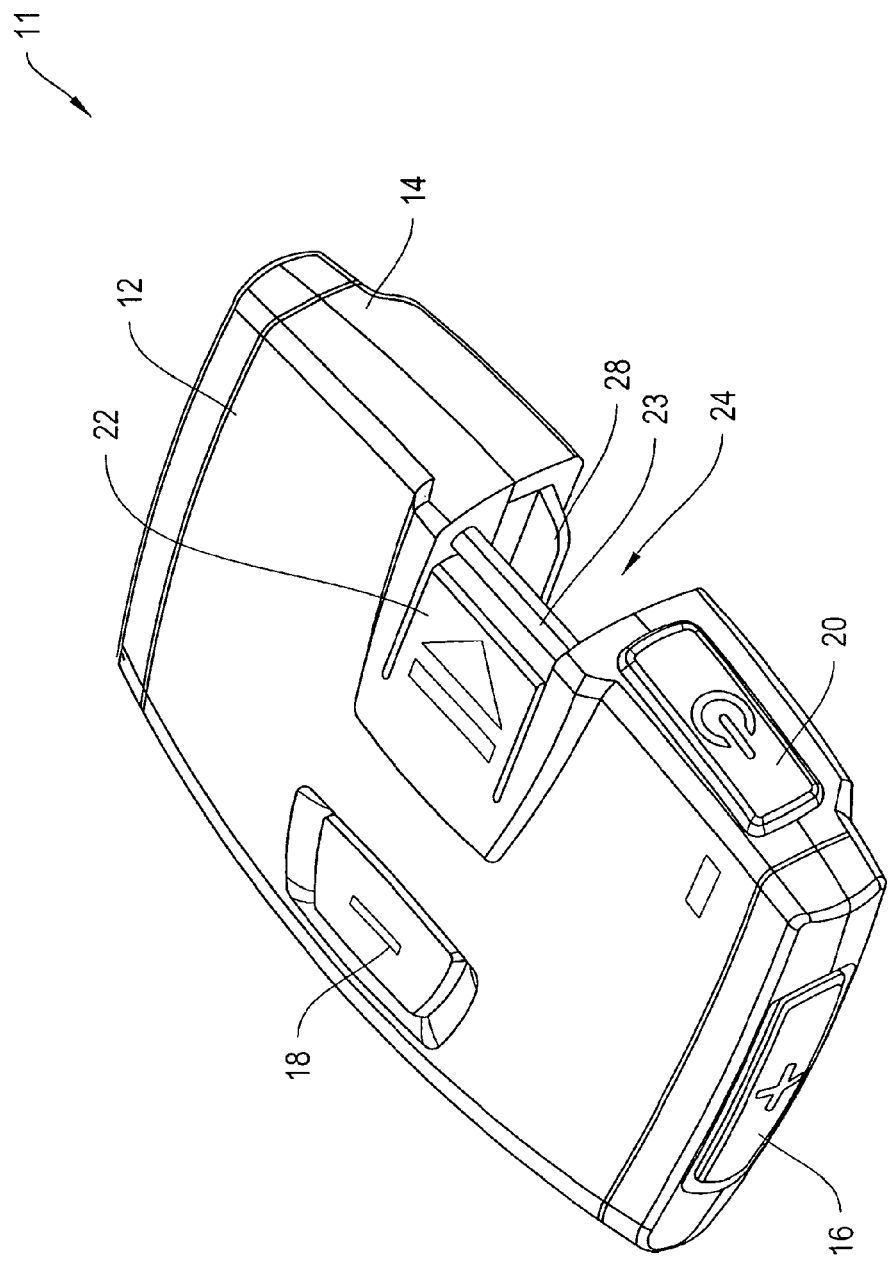
FIG. 2 is a perspective top view of the controller of the therapeutic electrical stimulation device shown in FIG. 1.
Figure 3:
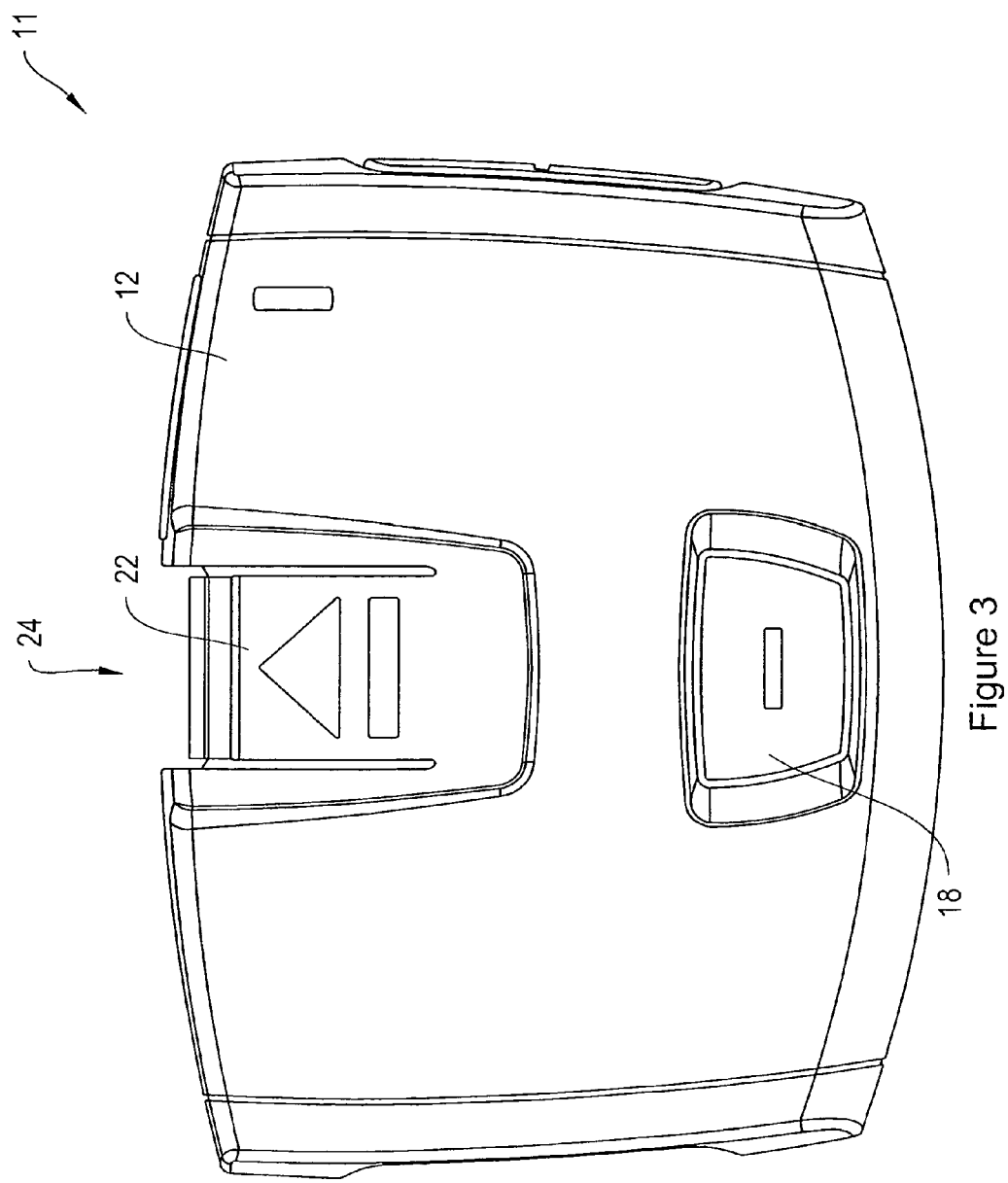
FIG. 3 is a top plan view of the controller of the therapeutic electrical stimulation device shown in FIG. 1.
Figure 4:
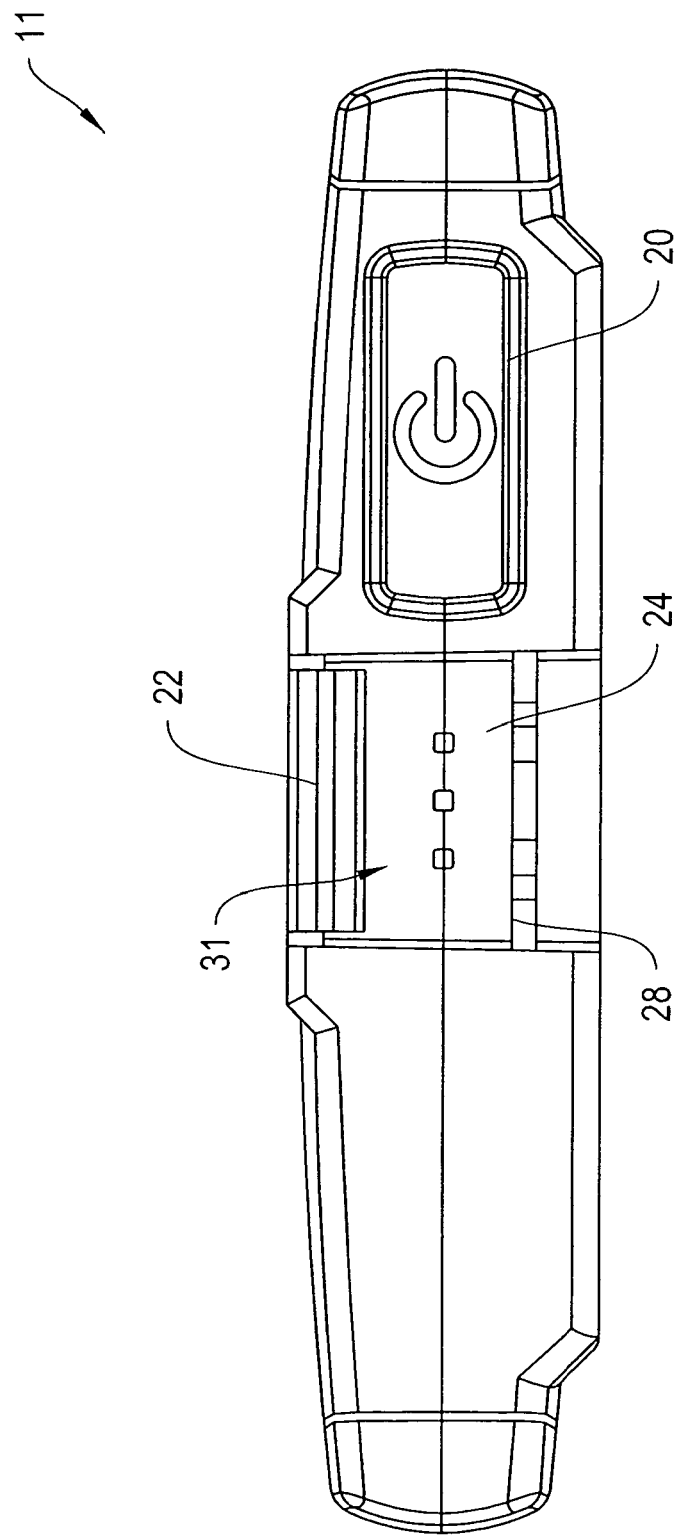
FIG. 4 is a front view of the controller of the therapeutic electrical stimulation device shown in FIG. 1.
Figure 5:
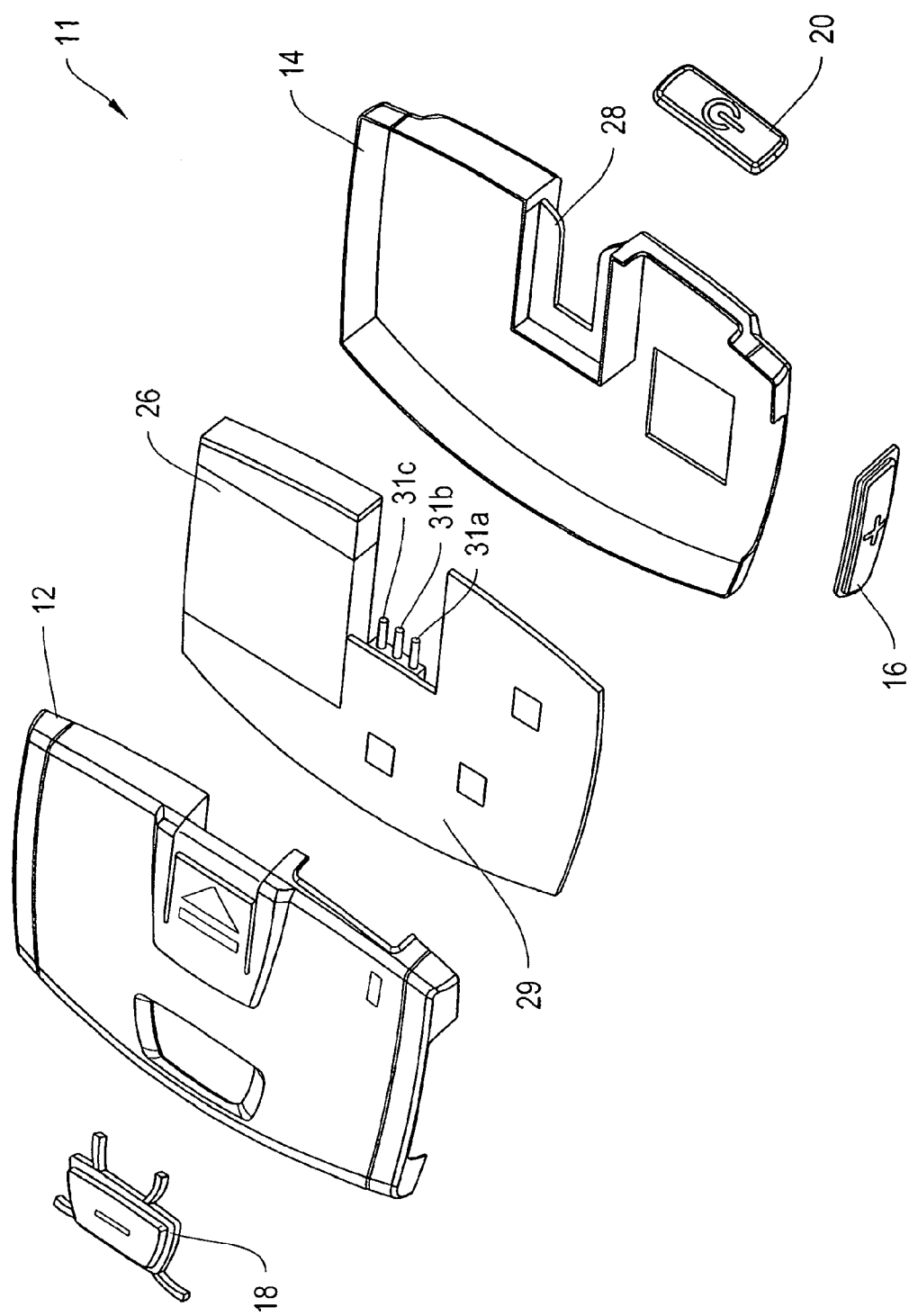
FIG. 5 is an exploded perspective view of the controller of the therapeutic electrical stimulation device shown in FIG. 1.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Referring now to FIG. 1, an example therapeutic electrical stimulation device 10 is shown. In this example, device 10 is a transcutaneous electrical nerve stimulation ("TENS")

device. Device 10 includes controller 11 and an electro-mechanical connecting shoe 13. Controller 11 generates electrical impulses and supplies the electrical impulses to shoe 13. The connector shoe 13 receives the electrical impulses from controller 11 and supplies the electrical impulses to a conductive layer or directly to a therapeutic location, such as the skin of a patient. Examples of electrical signals which may be used by controller 11 are described in more detail in U.S. Pat. No. 4,922,908, the teachings of which are incorporated herein by reference.

As shown in FIGS. 2-5, controller 11 includes an outer protective shell formed of upper housing 12 and lower housing 14. Upper and lower housings 12, 14 are made of any suitable material such as plastic, metal, or the like. A lower edge of upper housing 12 is configured to be connected with an upper edge of lower housing 14. In some embodiments, a fastener is used to connect upper housing 12 to lower housing 14. Examples of suitable fasteners include adhesive, screws, latching mechanisms, and other known fasteners. In other embodiments, upper housing 12 is directly connected to lower housing 14, such as by welding or over molding.

Upper and lower housings 12, 14 act together to enclose battery 26 and electrical circuitry 29. As a result, upper and lower housings 12, 14 provide protection to the enclosed components from contact with other objects that could otherwise damage the components. In some embodiments, upper and lower housings 12, 14 are water resistant to protect enclosed components from water or other fluids. Some embodiments of upper and lower housing 12, 14 are completely sealed to resist most or all fluid, gas, or particle intrusion. Some embodiments are hermetically sealed.

Battery 26 is a power source that provides electrical power to controller 11. In some embodiments, battery 26 is a rechargeable battery such as a lithium-ion battery. Battery 26 can be charged by connecting controller 11 to a battery charger, as described further below. One example of a battery charger is a docking station described in more detail herein. Inductive charging is used in some embodiments. In other embodiments, other rechargeable batteries are used, such as a nickel cadmium battery, a nickel metal hydride battery, or a rechargeable alkaline battery. Yet other embodiments include non-rechargeable, disposable batteries, such as alkaline batteries, or other known batteries. An alternate embodiment of controller 11 does not include battery 26, but rather includes a different power source such as a capacitor.

Lower housing 14 includes a controller receptacle 24 that is arranged and configured to receive a portion 42 of shoe 13. In some embodiments, lower housing 14 and portions of electrical circuitry 28 are uniquely arranged and configured to mate with portion 42 and resist mating with other shoe configurations. In addition, a railway platform 28 is positioned within controller receptacle 24 to fit with complementary surfaces on portion 42 to matingly engage with receptacle 24, as described more fully below. This mating engagement forms a keyed receptacle. One benefit of a keyed receptacle is that it can be used to resist connection with inappropriate patches or other devices, such as to resist connection with a patch that would be incompatible with controller 11. On the other hand, the keyed receptacle is also used in some embodiments to allow connection of controller 11 with various types of patches or other devices if desired.

In the example shown, the electrical circuitry 28 includes a PCB board 29 with a plurality of pins 31 extending therefrom. Pins 31 are sized to be received in receptacles formed in corresponding portion 42 of the shoe 13 to create an electrical connection between controller 11 and shoe 13, as described below.

Upper housing 12 includes a member 22 that moves into and out of controller receptacle 24 to capture and release corresponding structure 42 of the shoe 13. As described further below, as portion 42 is inserted into controller receptacle 24, and member 22 engages structure 56 on portion 42 to couple portion 42 to controller 11. To release portion 42, the user depresses member 22 to disengage member 22 from portion 56. Portion 42 of shoe 13 can then be pulled out of controller receptacle 24.

In one embodiment, controller 11 includes an on-board user interface having a power button 20 and amplitude adjustment buttons 16 and 18. When power button 20 is first depressed, the controller turns ON and begins generating therapeutic electrical signals. When power button 20 is depressed again, the controller turns OFF and stops generating the therapeutic electrical signals.

While the controller 11 is ON, amplitude adjustment buttons 16 and 18 are used to adjust the amplitude of the generated therapeutic electrical signals accordingly. Amplitude adjustment button 16 provides an input to increase ("+") the amplitude of the therapeutic electrical signals. Amplitude adjustment button 18 provides an input to decrease ("−") the amplitude of the therapeutic electrical signals.

Referring now to FIGS. 6-8B, the shoe 13, with sides 42a and 42b, is shown in greater detail. In the example shown, shoe 13 includes upper portion 42 and a base 44, having sides 44a and 44b. As shown, upper portion 42a is mounted to base portion 44a, and upper portion 442b is mounted to base portion 44b. Also typically included, but not shown, is an insulating layer (see, e.g., insulating layer 122 described below). During sliding insertion, portion 42 is configured to engage with a receptacle 24 (shown in FIGS. 9 and 10) of controller 11, as previously described. Portion 42 is a plastic or other suitable structure used to physically and electrically connect shoe 13 with controller 11.

Figure 8A:
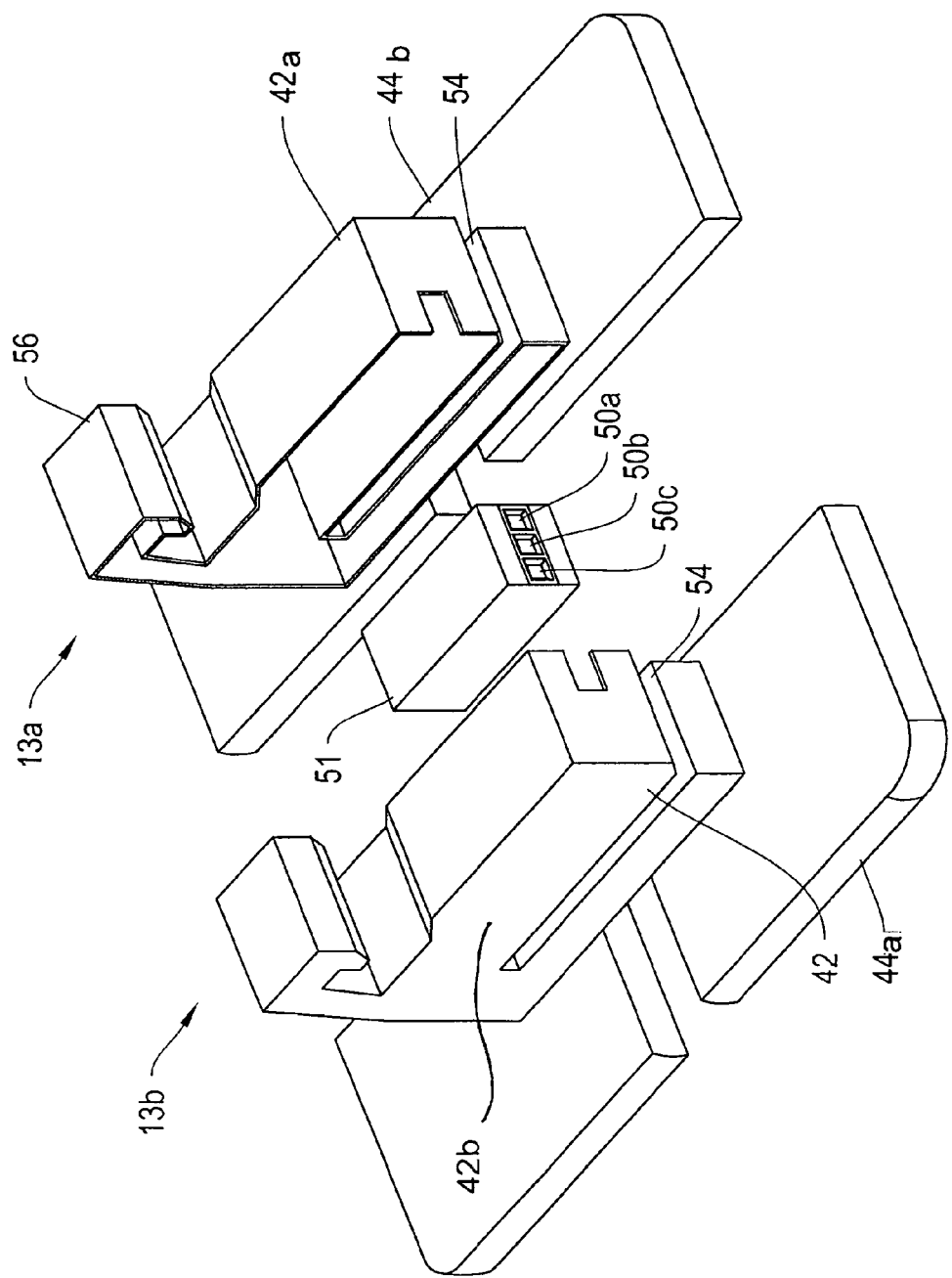
FIG. 8A is an exploded perspective view of a shoe of the therapeutic electrical stimulation device shown in FIG. 1.

The shoe 13 includes two symmetric halves 13a and 13b that allow insertion of an electrical connector 51 inside, as shown in FIG. 8A. The electrical connector may be any suitable electrical connection device, such as a FCI connector. The electrical connector 51 fits snugly inside of shoe 13 within the two halves. The electrical connector 51 may be fastened inside of the shoe 13 using glue, ultrasonic welding, or other available techniques.

One or more electrodes (such as electrodes 124 and 126 in FIG. 13 or electrodes 1502 in FIGS. 23B and 23D) are connected to shoe 13. When the electrodes are applied to a patient, they provide an electrical connection with the skin of the patient to supply electrical pulses to a desired therapeutic location, such as on the patient's skin. Exemplary electrodes are made of one or more sheets of electrically conductive material (e.g., conductive polymer or stainless steel). In some embodiments, the electrodes are generally disk-shaped to distribute the electrical signals across a relatively large area of skin. In other embodiments, the electrodes are of a variety of other shapes including ring-shaped, circular, elliptical, serpentine, comb-shaped, or other desired shape.

In operation, the electrodes are connected to the shoe 13 and ultimately to the controller using electrode lead wires 46, 48, which extend from shoe 13 and connect to the electrical connector 51. The connection of lead wires to the shoe and the electrodes is done using any appropriate connection mechanism (e.g., metal crimp, solder, etc.).

In certain embodiments, lead wire 46 connects to the shoe 13 through electrical connector 51 and to signal pin 31a in receptacle 50a. Lead wire 48 connects to the shoe 13 through electrical connector 51 and to ground pin 31b in receptacle 50b. Lead wire 46 and 48 connect to separate electrodes so that during stimulation, a voltage potential is generated between the electrodes and current enters the skin through one electrode, passes through the skin, and then returns through the other electrode.

A disposable, conducting adhesive layer (e.g., adhesive layer 128 and 1504 described below) is applied to one side of electrodes 124, 126 and 1502 to allow the electrodes to be securely, yet removably, adhered to the skin and to permit the electrical signals to flow from the controller 11 to the patient. In some embodiments, adhesive layers 128 and 1504 are applied across an entire surface of electrodes 124, 126 and 1502. In other embodiments, adhesive layers 128 and 1504 are electrically connected to the shoe, but not to the regions of electrodes 124, 126 and 1502. Other adhesive layer arrangements are used in other embodiments. Exemplary adhesive layers are made of an electrically conductive material such as an electrogel or hydrogel (e.g., UltraStim Self-Adhering Neurostimulation Electrodes made by Axelgaard Manufacturing Co.). The adhesive layer is preferably disposed of after one use, but may reused for multiple applications. Some embodiments of shoe 13 include additional layers.

During stimulation, controller 11 generates a voltage potential between electrode lead wires 46, 48 such that the current enters the skin through one wire, passes through the skin, and then returns through the other wire. Some embodiments provide a plurality of electrodes. In some implementations, the polarity of the electrodes is alternated during a therapy. In some embodiments a skin preparation product, such as a conductive gel, is applied to the skin prior to application of shoe 13.

To make electrical connection between shoe 13 and controller 11, portion 42 includes a plurality of receptacles 50a-50c on a front face 52 of portion 42. The receptacles are part of connector 51 (e.g., FCI connector) housed inside of shoe 13. The three electrical receptacles 50a-50c are assigned various functions such as providing an electrical signal, connection to ground, and battery charging connection. The electrical receptacles 50a-50c are sized to receive pins 31a-31c, respectively, of controller 11 when portion 42 is fully inserted into connector receptacle 24 (see FIGS. 9 and 10), and provide a location where the pins 31a and 31b connect with the lead wires 46 and 48, respectively. As shown, pins 31 extend generally parallel to the railway platform 28.

Fitting pins 31 into receptacles 50 creates an electrical connection between controller 11 and shoe 13 and allows controller 11 to deliver electrical stimulation therapy through electrode lines 46, 48 to the patient. In particular, as shown, receptacle 50a receives the electrical signal pin 31a and receptacle 50b receives the ground pin 31b, which combine to form the electrical connection between the shoe 13 and the controller 11. Receptacle 50c receives the battery charging pin 31c. It will be appreciated that when the shoe 13 and the controller 11 are mated together for operation, the battery charging pin 31c sits within the receptacle 50c but does not electrically connect. As discussed below, the controller 11 may be disengaged from the shoe 13 after patient therapy and connected to a battery charging station.

Figure 6:
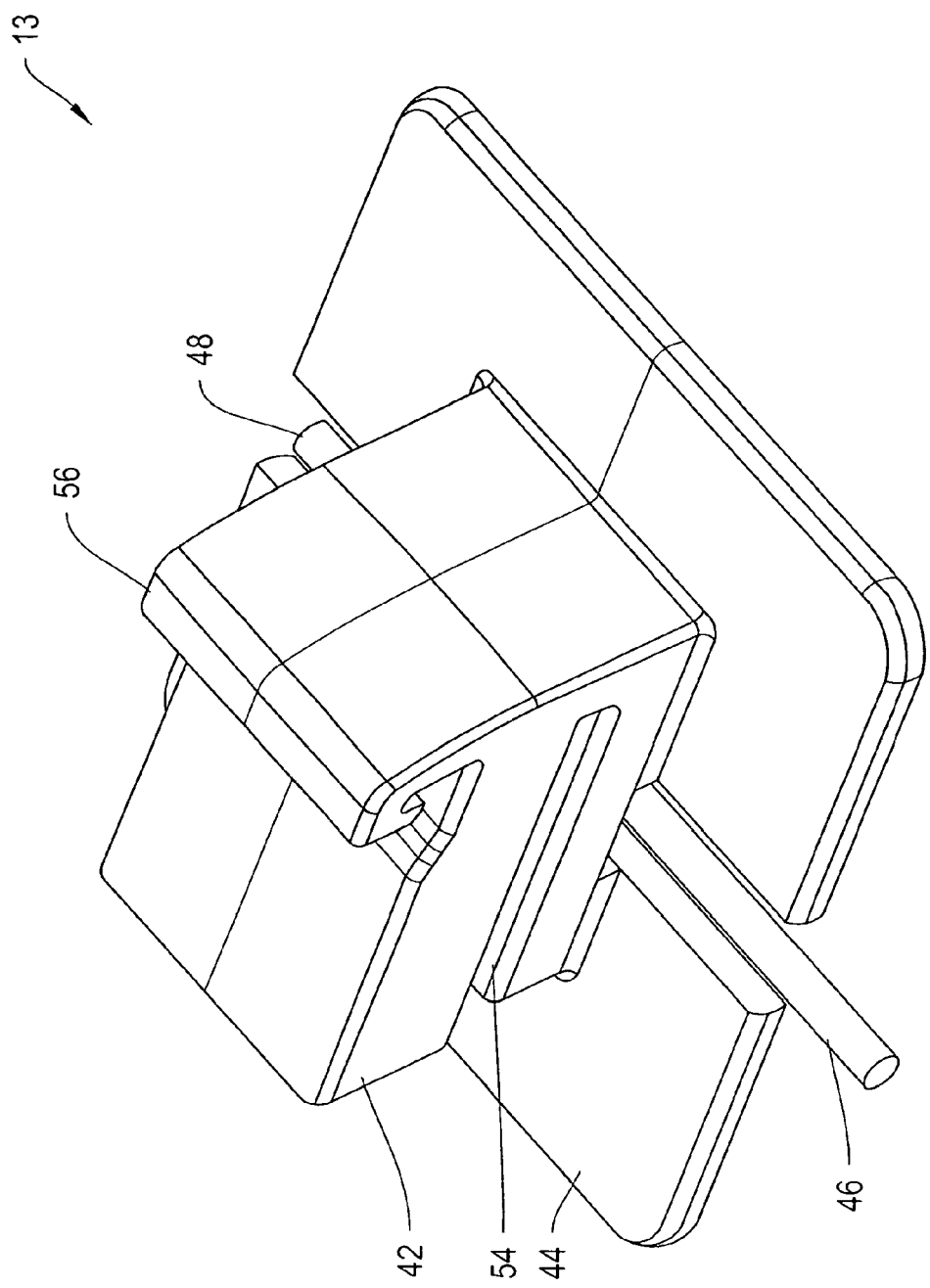
FIG. 6 is a perspective top view of a shoe of the therapeutic electrical stimulation device shown in FIG. 1.

The mechanical connection between the shoe 13 and controller 11 is further shown in FIGS. 6-10B. With reference to FIG. 6, shoe 13 includes portion 42 that defines a channel 54 sized to receive railway platform 28 of controller 11 when portion 42 is inserted into controller receptacle 24. Railway platform 28 slides inside channel 54 below portion 42 and above the bottom surface defining channel 54, fitting in a 'U' shape around portion 55 of shoe 13. Also, portion 42 includes a clip member 56 sized to engage a detent or lip 23 of member 22 of controller 11 when portion 42 is fully inserted into controller receptacle 24 to retain portion 42 within receptacle 24. In certain embodiments, when clip member 56 engages the lip 23 of member 22 the connection creates an affirmative "click" sound, indicating that shoe 13 is connected to controller 11. In addition, the base 44 of the shoe includes two side flanges 44a and 44b. As the shoe 13 slides into connection with the controller 11, the base flanges 44a and 44b slide under and at least partially abut respective side portions 8a and 8b of the controller 11.

Figure 9:
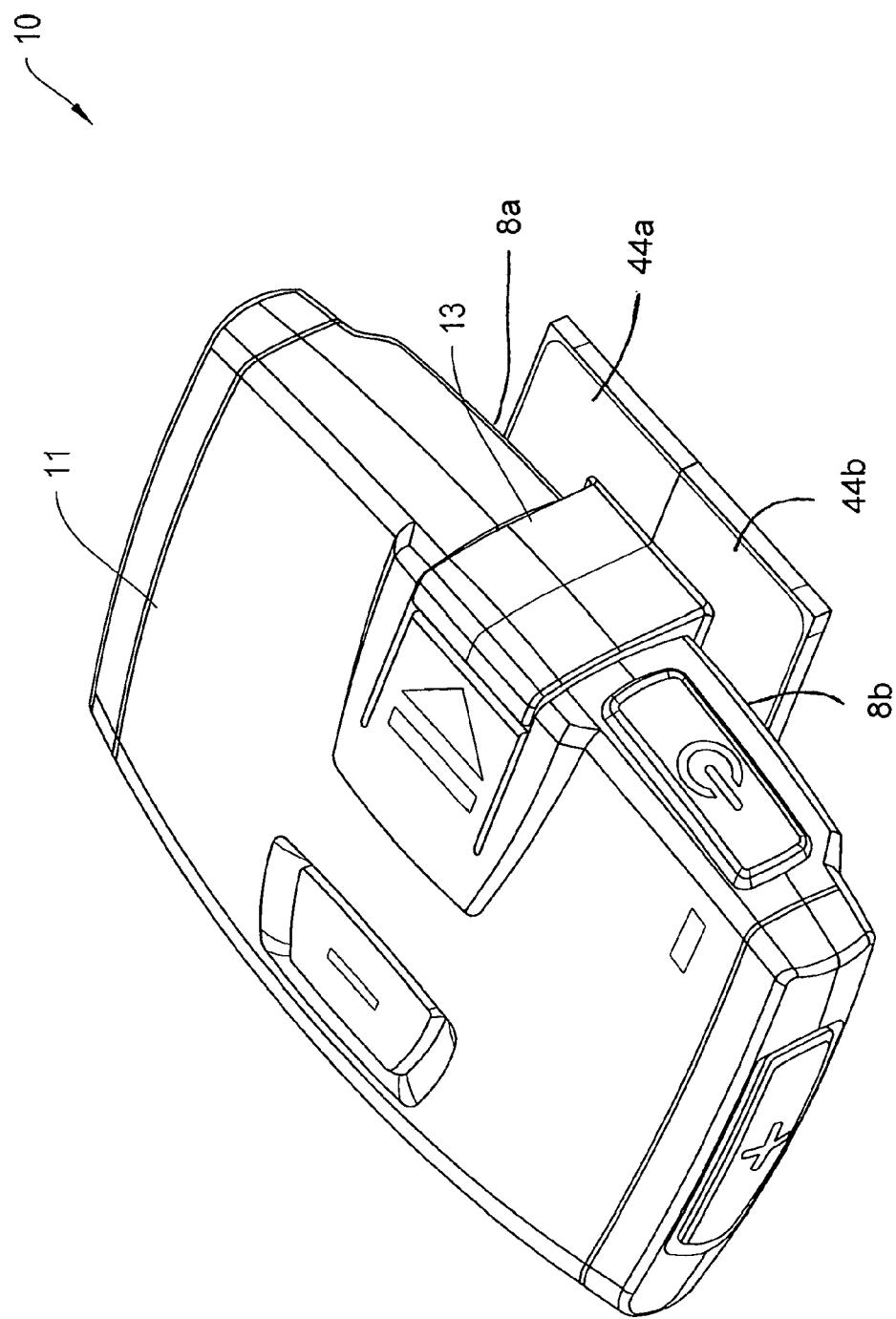
FIG. 9 is a perspective view of the therapeutic electrical stimulation device shown in FIG. 1.
Figure 10A:
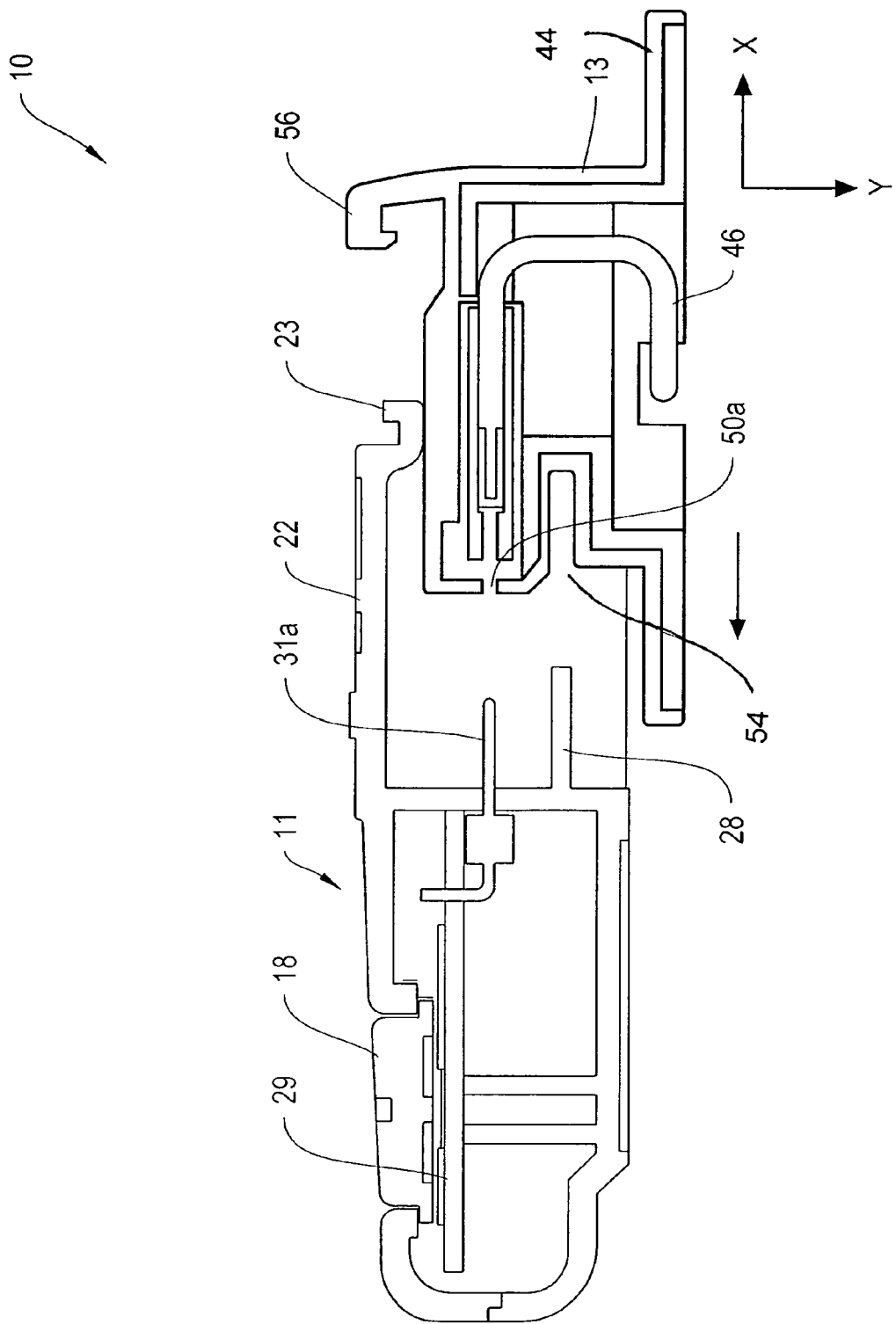
FIG. 10A is a side cross-sectional view of the therapeutic electrical stimulation device before connection.
Figure 10B:
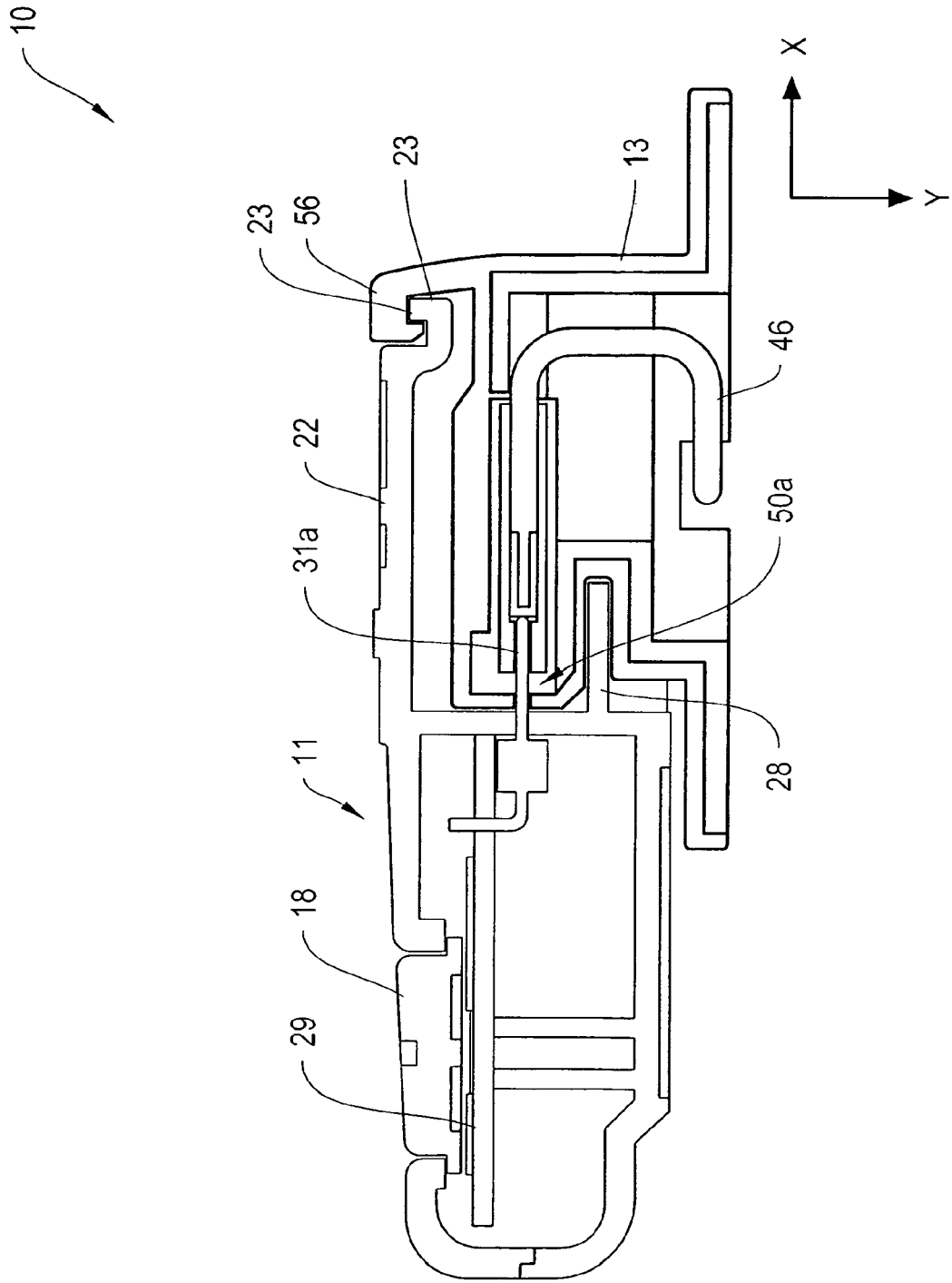
FIG. 10B is a side cross-sectional view of the therapeutic electrical stimulation device shown in FIG. 9 after connection.

Referring now to FIGS. 9 and 10B, the coupling between shoe 13 and controller 11 also occurs as pins 31 of controller 11 are inserted into receptacles 50 of portion 42 of shoe 13.

The process of connecting shoe 13 and controller 11 begins as shown in FIG. 10A which depicts the controller 11 and shoe 13 detached and in position to be coupled. By moving shoe 13 in the direction X (i.e., in the direction of the arrow toward controller 11), they can be coupled as shown in FIGS. 9 and 10B.

When coupled, railway 28 of controller 11 is received in channel 54 of portion 42 and allows portion 42 to be slid along railway 28 as portion 42 is inserted into controller receptacle 24. Additionally, railway 28 fits around portion 55 of shoe 13. The engagement of railway 28 and channel 54 fixes the position of controller 11 and shoe 13 in a direction Y so that shoe 13 cannot be moved out of controller receptacle 24 in the direction Y.

Further, lip 23 of member 22 of controller 11 is engaged by clip member 56 of portion 42. The engagement of lip 23 and clip member 56 fixes the position of controller 11 and shoe 13 in a second dimension so that shoe 13 cannot be moved in a direction X out of controller receptacle 24. When the user wants to remove portion 42 from controller receptacle 24, the user depresses member 22 in the direction Y so that lip 23 clears clip member 56. Portion 42 thereupon be slid along railway 28 in direction X out of receptacle 24. Flanges 44a and 44b engage portions 8a and 8b, as described above.

Other configurations can be used to maintain the portion 42 in the receptacle 24. For example, in another embodiment, a knob or knurl can be formed on the portion 42 that engages or is seated with a detent within the receptacle when fully inserted. When the portion 42 is removed, the knob or knurl flexes slightly to bend away from the detent so that the portion can be removed. Other configurations are possible.

In some examples described herein, shoe 13 is connected to a garment to deliver therapy to the user. The is made by stitching, gluing or embedding the shoe 13 in a laminate layer. In other examples, shoe 13 is connected to other structures to deliver therapy; charge controller 11; and/or program controller 11.

Figure 11:
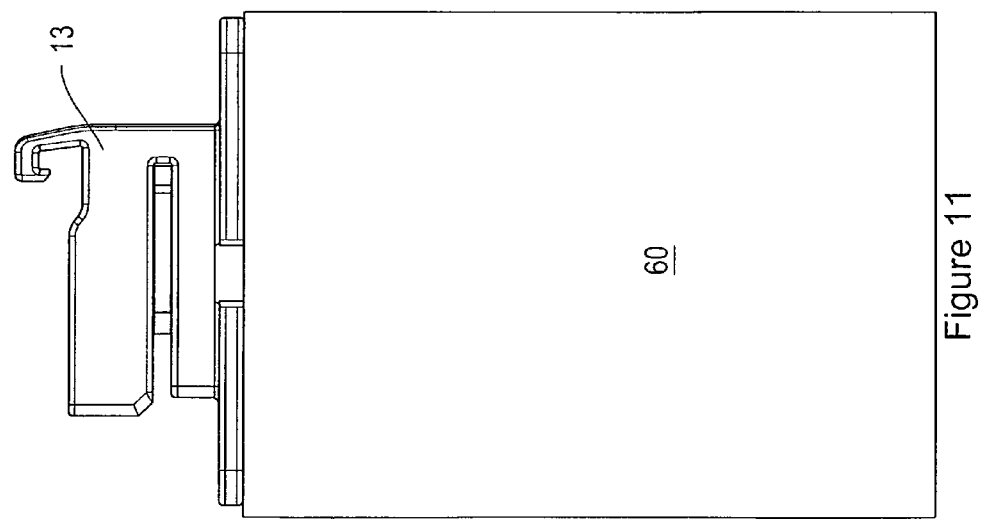
FIG. 11 is a block diagram of an example shoe of the therapeutic electrical stimulation device shown in FIG. 1 attached to a generic structure.

For example, referring now to FIG. 11, shoe 13 is electrically connected to a structure 60. As described below, shoe 13 can be connected to a plurality of different structures so that controller 11 can be coupled thereto.

In some examples, structure 60 is an apparatus that can be used to deliver therapy to the user. For example, as described below, structure 60 can be a patch (e.g., patch 104) or an electrode that is attached to the skin to deliver therapy. In other examples, structure 60 is a garment such as a belt that is worn around certain anatomy of a patient, such as the waist, arm, or leg. One or more shoes 13 can be located along the belt so that one or more controllers 11 can be coupled to the shoes 13 to deliver therapy at desired locations along the belt. For example, the belt can include a single shoe 13 for one controller 11, and can include a plurality of electrodes that are spaced along the belt to deliver therapy along an entire surface for the patient. FIG. 23D shows an example of a belt including a shoe 13 with base 44 electrically connected to electrodes

1502. Electrodes 1502 may be placed in any position along the belt and in any pattern suitable to provide therapy to a user. There may be an array of four electrodes, as shown in FIG. 23D, or there may be more or fewer electrodes provided as necessary. In addition, multiple shoes 13, may be placed on the belt of FIG. 23D. In other examples, structure 60 is a brace or cast (e.g., air cast, knee brace, or back brace) with built-in electrodes that allow controller 11 to be connected to the shoe and delivery therapy to the desired area.

In some embodiments, structure 60 is electrical components that are used to provide power so that controller 11 can be connected to shoe 13 to charge battery 26 in controller 11. For example, in one embodiment, structure 60 is a docking station, such as docking station 1300 described below. In other examples, structure 60 is an electrical power transformer that can be plugged into a typical wall outlet or an automobile outlet to provide power to charge battery 26. In other examples, controller 11 can also include an auxiliary charging port, such as a USB or micro-USB port, which can be used to charge controller 11. In yet other examples, controller 11 can include on-board recharge capabilities, such as solar panels or inductive coupling technologies.

In yet other examples, structure 60 is electrical circuitry that can be used to program controller 11. In some embodiments, controller 11 includes computer readable media, such as RAM or ROM. In one embodiment, controller 11 includes flash memory that can be rewritten with new therapy programs to enhance the functionality of controller 11.

In such examples, structure 60 can be a docking station, such as docking station 1300 described below. In other examples, structure 60 can be a component in a care giver's office that allows the care giver to modify or enhance the therapies that can be provided by controller 11. In other examples structure 60 can be connected to a LAN or have an Internet or phone connection.

Figure 12:
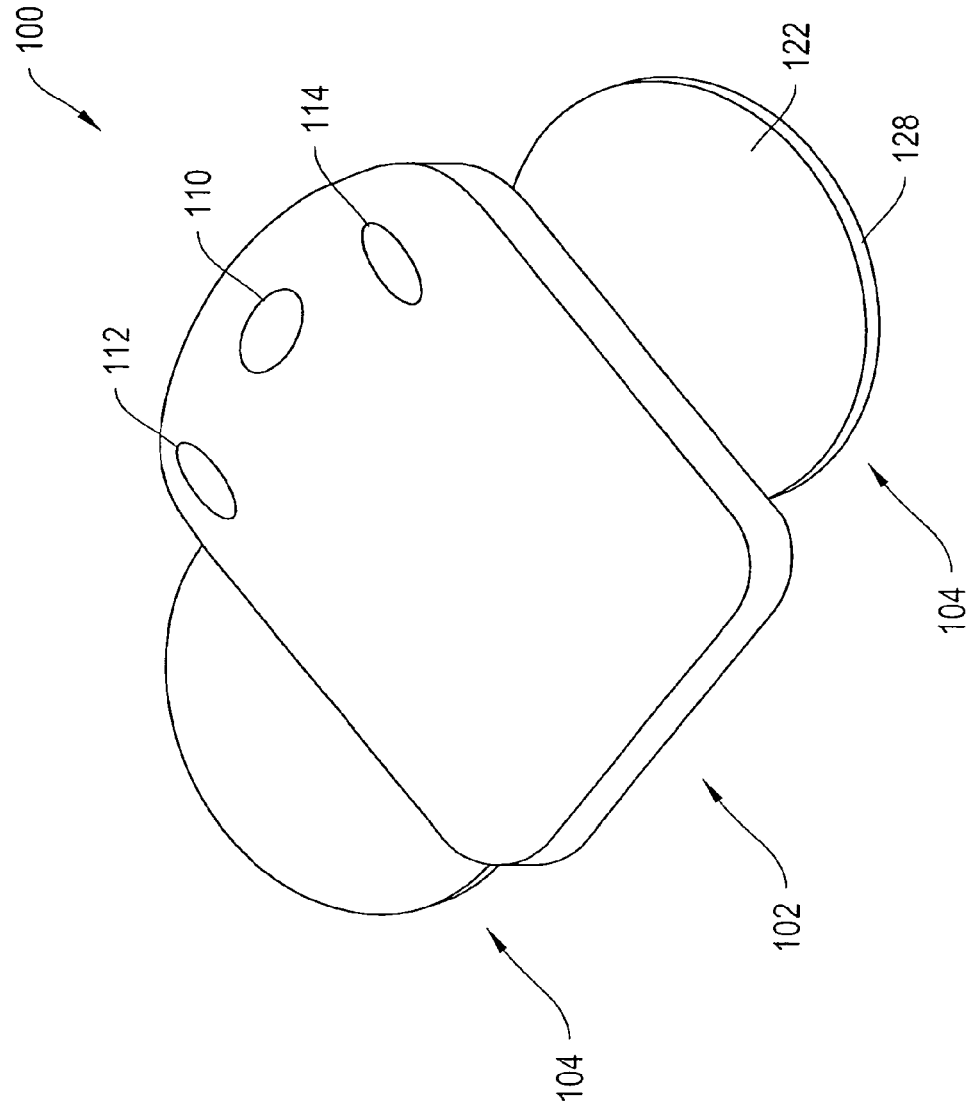
FIG. 12 is a perspective top view of another example therapeutic electrical stimulation device.

Referring now to FIG. 12, another example therapeutic electrical stimulation device 100 is shown. Device 100 is similar to device 10 described above, except that device 100 is configured differently. In the example of FIG. 12, device 100 is a transcutaneous electrical nerve stimulation ("TENS") device. Device 100 includes controller 102 and patch 104, similar to those described above. Controller 102 is a device that generates electrical impulses and supplies the electrical impulses to patch 104. Patch 104 receives the electrical impulses from controller 102 and supplies the electrical impulses to a therapeutic location, such as the skin of a patient.

In one embodiment, controller 102 includes a user interface having a power button 110 and amplitude adjustment buttons 112 and 114. When power button 110 is first depressed, the controller turns ON and begins generating therapeutic electrical signals. When power button 110 is depressed again, the controller turns OFF and stops generating the therapeutic electrical signals.

While the controller 102 is ON, amplitude adjustment buttons 112 and 114 are used to adjust the amplitude of the generated therapeutic electrical signals accordingly. Amplitude adjustment button 112 provides an input to increase the amplitude of the therapeutic electrical signals. Amplitude adjustment button 114 provides an input to decrease the amplitude of the therapeutic electrical signals.

Patch 104 is typically applied to the skin of a patient. The electrical signals are conducted from the controller to the skin by patch 104. Patch 104 includes a shoe 120 (shown in FIG. 13), an insulating layer 122, and conductive electrodes 124 and 126. Shoe 120 is connected to one side of insulating layer 122, and is configured to engage with a receptacle (shown in FIG. 14) of controller 102. Shoe 120 is a connector used to physically and electrically connect patch 104 with controller 102.

Electrodes 124 and 126 (shown more clearly in FIG. 13) are located adjacent insulating layer 122 on a side opposite shoe 120. The electrodes are typically a sheet of electrically conductive material that, when applied to a patient, provides an electrical connection with the skin of the patient to supply electrical pulses to a desired therapeutic location. An adhesive layer 128 is typically applied to one side of patch 104 to allow patch 104 to be securely, yet removably, adhered to the skin. Some embodiments of patch 104 include additional layers.

During stimulation, controller 102 typically generates a voltage potential between electrodes 124 and 126 such that current enters the skin through one electrode, passes through the skin, and then returns through the other electrode. Some embodiments alternate the polarity of the electrodes during a therapy. In some embodiments a skin preparation product, such as a conductive gel, is applied to the skin prior to application of patch 104.

In some embodiments, buttons 110, 112, and 114 are arranged with a unique tactile arrangement. For example, buttons 110, 112, and 114 are arranged at one end of controller 102 and protrude out from the housing of controller 102. The tactile arrangement allows the device to be controlled by the patient or caregiver even if the device is hidden from view under clothing or in a non-visible location, such as on the back. If, for example, the device is located under a shirt on the patient's upper arm, the patient can feel controller 102 through the shirt and locate protruding buttons 110, 112, and 114. Due to the unique arrangement of buttons 110, 112, and 114, the user is able to identify each button, and select from them accordingly. Other embodiments include additional tactile elements. For example, in some embodiments buttons 110, 112, and 114 include an elevated identifier, such as a line, square, arrow, dot, circle, or Braille character. In other embodiments, buttons 110, 112, and 114 each include a unique shape, such as a square, triangle, circle, oval, rectangle, arrow, or other desired shape. In yet other embodiments, buttons are located on different locations of the housing, such as on the sides or bottom of the housing.

Figure 13:
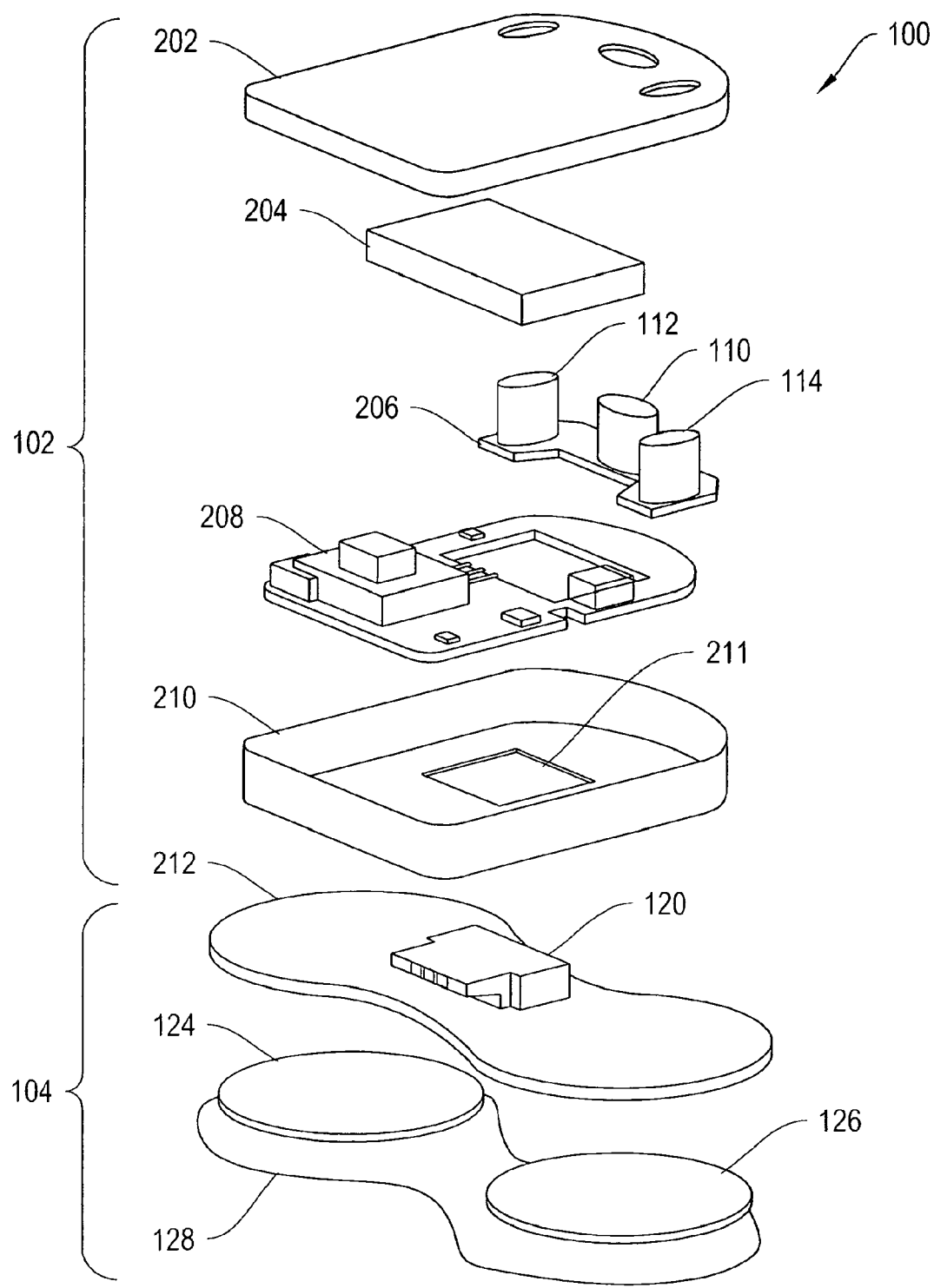
FIG. 13 is an exploded perspective view of the therapeutic electrical stimulation device shown in FIG. 12.

FIG. 13 is an exploded perspective view exemplary therapeutic electrical stimulation device 100. Device 100 includes controller 102 and patch 104. Controller 102 includes upper housing 202, battery 204, user input devices 206, electrical circuitry 208, and lower housing 210. Patch 104 includes shoe 120, insulating layer 212, electrodes 124 and 126, and adhesive layer 128.

Controller 102 includes an outer protective shell formed of upper housing 202 and lower housing 210. Upper and lower housings 202 and 210 are made of any suitable material such as plastic, metal, or the like. A lower edge of upper housing 202 is configured to be connected with an upper edge of lower housing 210. In some embodiments, a fastener is used to connect upper housing 202 to lower housing 210. Examples of suitable fasteners include adhesive, screws, latching mechanisms, and other known fasteners. In other embodiments, upper housing 202 is directly connected to lower housing 210, such as by welding or over molding.

Upper and lower housings 202 and 210 act together to enclose battery 204 and electrical circuitry 208 and to at least partially enclose user input devices 206. As a result, upper and lower housings 202 and 210 provide protection to the enclosed components from contact with other objects that could otherwise damage the components. In some embodiments, upper and lower housings 202 and 210 are water resistant to protect enclosed components from water or other fluids. Some embodiments of upper and lower housing 202 and 210 are completely sealed to resist most or all fluid, gas, or particle intrusion. Some embodiments are hermetically sealed.

Lower housing 210 includes a controller receptacle 211 that is arranged and configured to receive shoe 120 of patch 104. In some embodiments, lower housing 210 and portions of electrical circuitry 208 are uniquely arranged and configured to mate with shoe 120 and resist mating with other shoe configurations. This is sometimes referred to as a keyed receptacle. One benefit of a keyed receptacle is that it can be used to resist connection with inappropriate patches or other devices, such as to resist connection with a patch that would be incompatible with controller 102. On the other hand, the keyed receptacle is also used in some embodiments to allow connection of controller 102 with various types of patches or other devices if desired.

Battery 204 is a power source that provides electrical power to controller 102. In some embodiments, battery 204 is a rechargeable battery such as a lithium-ion battery. Battery 204 can be charged by connecting controller 102 to a battery charger. One example of a battery charger is a docking station described in more detail herein. Inductive charging is used in some embodiments. In other embodiments, other rechargeable batteries are used, such as a nickel cadmium battery, a nickel metal hydride battery, or a rechargeable alkaline battery. Yet other embodiments include non-rechargeable, disposable batteries, such as alkaline batteries, or other known batteries. An alternate embodiment of controller 102 does not include battery 204, but rather includes a different power source such as a capacitor.

User input devices 206 receive input from a user to cause controller 102 to adjust an operational mode of the device 100. Different operational modes may be used to provide different types of therapy, such as therapy to treat edema or to provide drug delivery. A more thorough description of how operational modes work can be found in U.S. Pat. No. 5,961,542 which is incorporated herein by reference. User input devices 206 include power button 110 and amplitude adjustment buttons 112 and 114. User input devices 206 are arranged such that a portion of buttons 110, 112, and 114 protrude through upper housing 202. A user provides input to controller 102 by momentarily depressing one of buttons 110, 112, and 114. When the button is depressed, the force is transferred through user input device 206 to a switch of electrical circuitry 208. The switch closes to make an electrical connection and causes current flow within electrical circuitry 208. The electrical circuitry 208 responds to adjust the appropriate operational mode of controller 102.

Electrical circuitry 208 typically includes a circuit board and a plurality of electrical circuits such as a power supply circuit, pulse generator circuit, and electrical contacts for electrical connection with conductors of shoe 120. Examples of electrical circuitry 208 are described in more detail herein. In some embodiments, electrical circuitry 208 includes sensors that receive electrical signals from patch 104. In some embodiments the electrical circuitry is activated between output pulses to monitor the patient. Some embodiments of controller 102 further include sensor electronics that monitor patch 104 to be sure that patch has not become partially or fully disconnected from the patient. If the patch does become disconnected, the electronics deactivate delivery of therapeutic electrical signals from controller 102. A more detailed description of how a patch connection can be monitored is found in U.S. Patent Application Publication No. 2004/0015212, which is incorporated herein by reference. In some embodiments, the electronics monitor for changes in impedance between electrodes. In another embodiment, electrical circuitry 208 also includes activity monitoring, such as with an accelerometer. With activity monitoring, feedback control is used to increase electrical stimulation level in response to activity level.

Patch 104 is a device that transfers electrical impulses from controller 102 to a therapeutic location on a patient, such as the patient's skin. Patch 104 includes shoe 120, insulating layer 212, electrodes 124 and 126, and adhesive layer 128.

Shoe 120 is arranged and configured to engage with controller 102, such as through controller receptacle 211. In some embodiments, shoe 120 includes a unique configuration that is designed to mate only with controller receptacle 211 and to resist connection with other receptacles or devices. The unique configuration is sometimes referred to as a keyed shoe. One benefit of a keyed shoe is that it can be used to resist connection with inappropriate controllers or other devices, such as to resist connection with a controller that would be incompatible with patch 104. This may be done by creating a unique shoe configuration with a particular two or three dimensional shape that fits snugly within controller receptacle 211. Thus, controller receptacles and shoes that do not have a matching two or three dimensional shape cannot be connected. On the other hand, the keyed shoe is also used in some embodiments to allow patch 104 to be connected with various types of controller 102. In this case, the shoe may be designed with a two or three dimensional shape that fits into multiple controller receptacles. Shoe 120 includes conductors that conduct electrical signals between controller 102 and electrodes 124 and 126.

Patch 104 includes insulating layer 212. Insulating layer 212 is connected to patch 104 by any suitable fastening mechanism, such as adhesive, screws, nails, or other known fasteners. In other embodiments, insulating layer 212 and shoe 120 are formed of a unitary piece, such as by molding. Conductors from shoe 120 pass from shoe 120, through insulating layer 212, and are connected to electrodes 124 and 126.

In some embodiments, insulating layer 212 is a primary structural layer of patch 104. Insulating layer 212 also electrically insulates a side of patch 104. In this way, if insulating layer 212 comes into contact with a conductive object (e.g., the hand of the patient or another electronic device), insulating layer 212 prevents or at least resists the electrical conduction between electrodes 124 and 126 and the conductive object. Inadvertent electrical shocks and unintended electrical connections are thereby reduced or entirely prevented.

Electrodes 124 and 126 are electrical conductors that are used to introduce electrical signals to a therapeutic location of a patient, such as on to the patient's skin. Electrodes 124 and 126 are electrically connected to conductors that pass through shoe 120. In some embodiments electrodes 124 and 126 are generally disk-shaped to distribute the electrical signals across a relatively large area of skin. In other embodiments, electrodes 124 and 126 are of a variety of other shapes including ring-shaped, circular, elliptical, serpentine, comb-shaped, or other desired shape.

Patch 104 is connected to the skin of a patient with adhesive layer 128. In some embodiments, adhesive layer 128 is applied across an entire surface of patch 104, including across electrodes 124 and 126. In such embodiments, adhesive layer 128 is electrically conductive. In other embodiments, adhesive layer 128 is applied to the surface of patch 104, but not on the regions of electrodes 124 and 126. Other adhesive layer arrangements are used in other embodiments.

Figure 14:
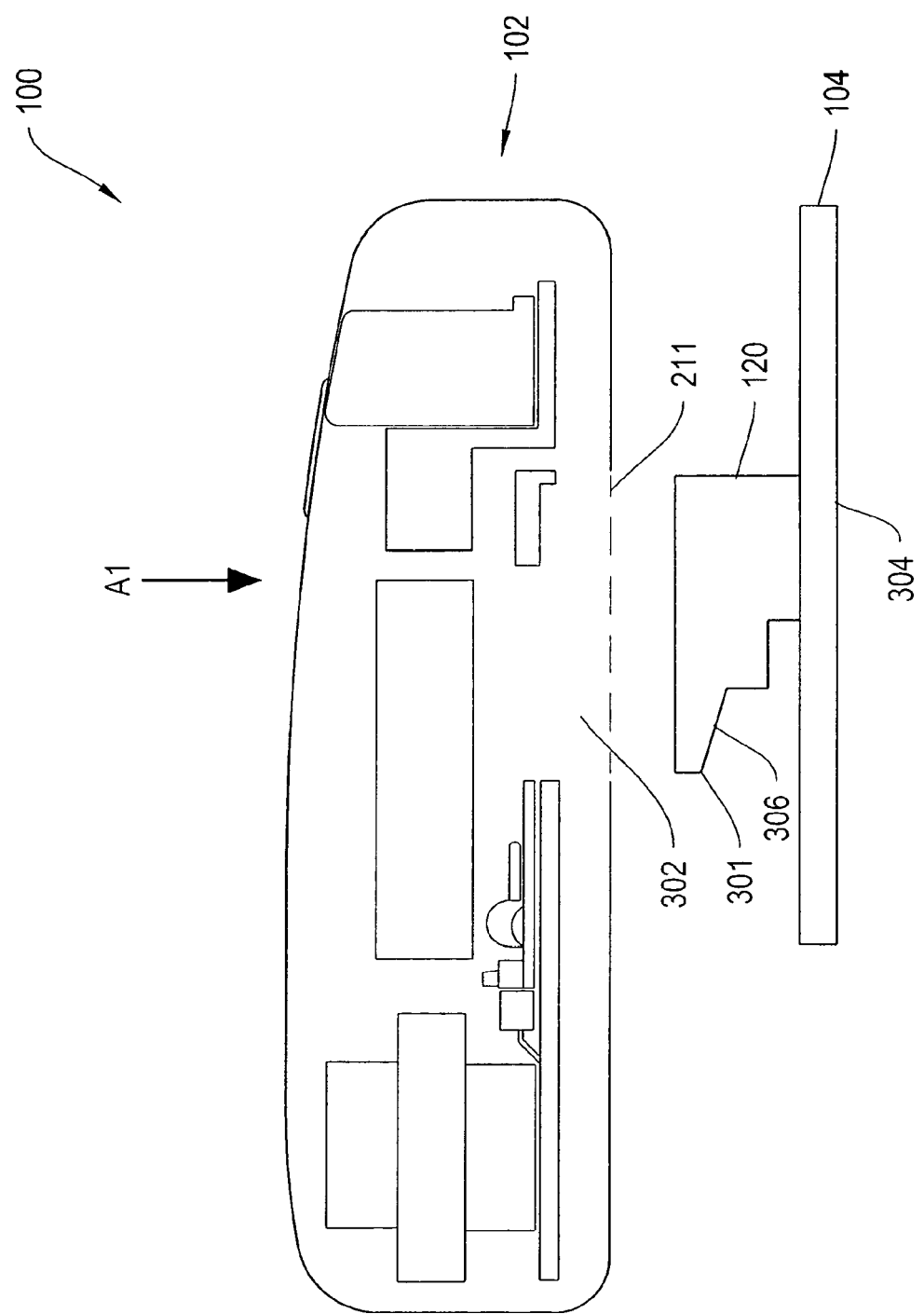
FIG. 14 is a right side cross-sectional view of the device shown in FIG. 12, including a controller that is disconnected from a patch.
Figure 15:
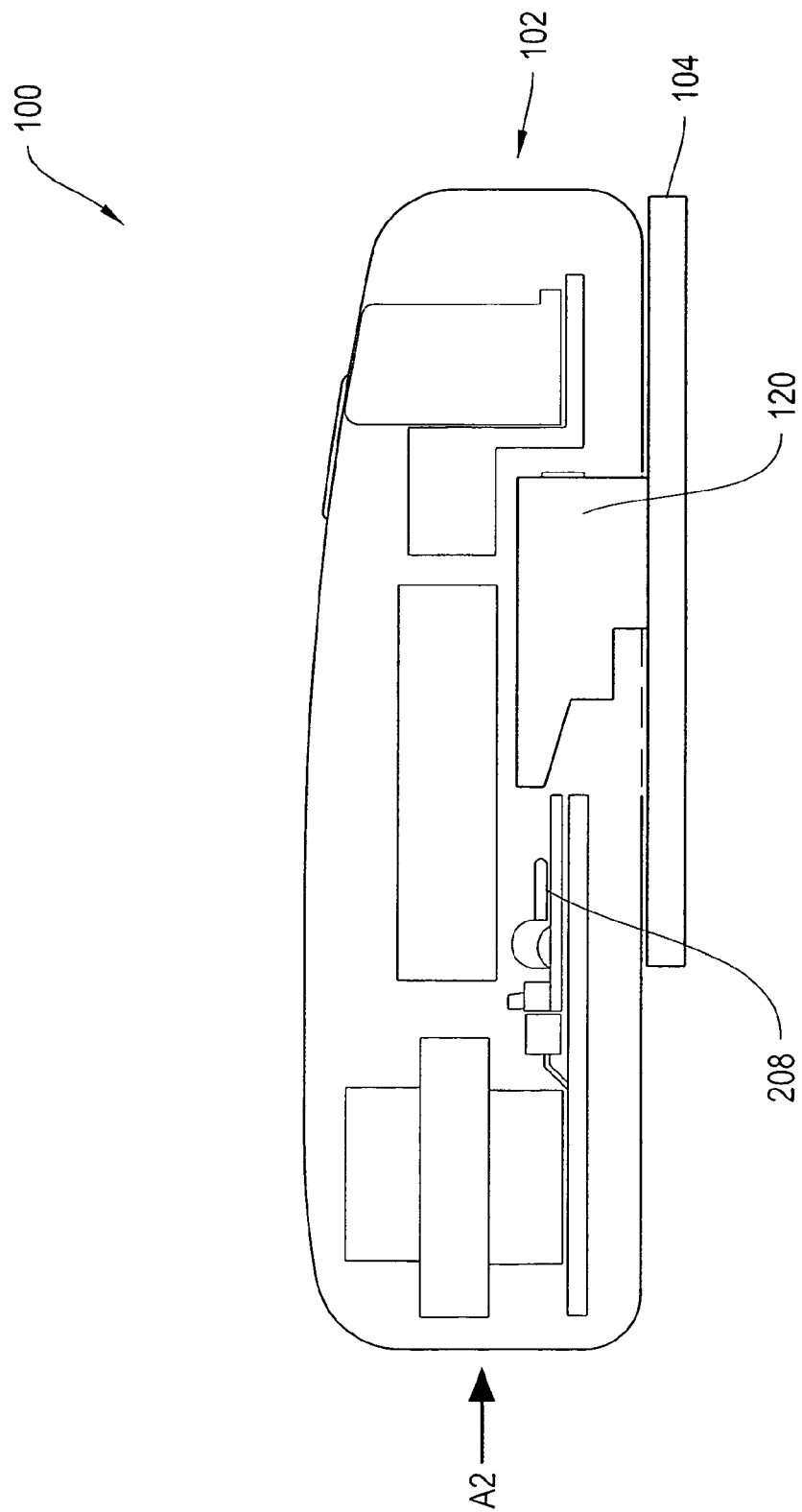
FIG. 15 is a right side cross-sectional view of the device shown in FIG. 14 with the controller being arranged over the patch.
Figure 16:
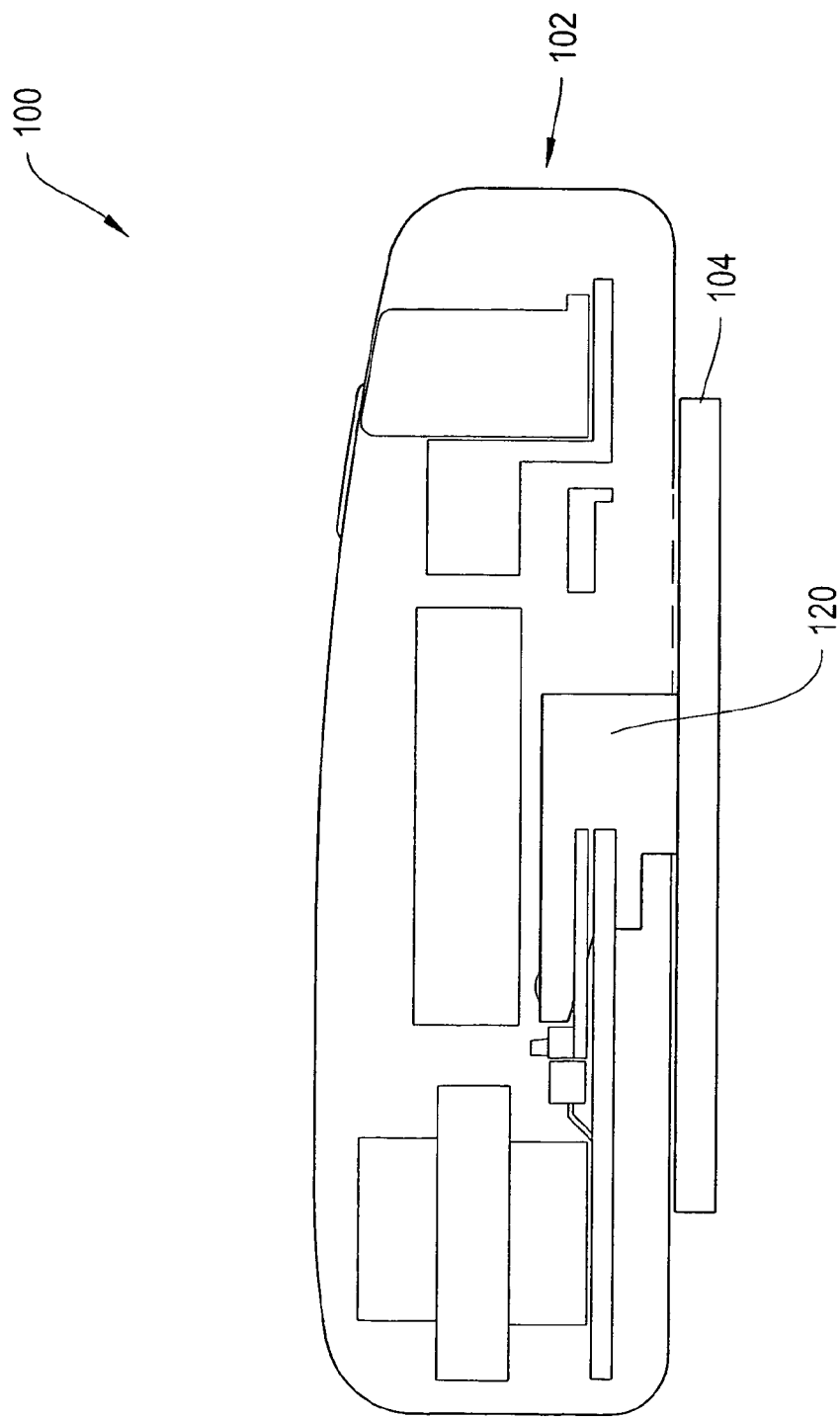
FIG. 16 is a right side cross-sectional view of the device shown in FIG. 14 with the controller being connected with the patch.

FIGS. 14-16 illustrate an exemplary method of connecting a controller 102 to a patch 104 of a therapeutic electrical stimulation device 100. FIGS. 14-16 are right side cross-sectional views of device 100. FIG. 14 illustrates controller 102 disconnected from patch 104. FIG. 15 illustrates controller 102 arranged in a first position over patch 104. FIG. 16 illustrates controller 102 arranged in a second position and connected with patch 104. A method of disconnecting controller 102 from patch 104 is the reverse of that described herein.

Before connecting controller 102 with patch 104, patch 104 is typically applied to a desired therapeutic location on the patient (not shown in FIG. 14) such that shoe 120 extends from patch 104 in a direction generally away from the therapeutic location.

The process of connecting controller 102 with patch 104 begins as illustrated in FIG. 14, such that controller 102 is arranged such that controller receptacle 211 is in line with shoe 120. Controller 102 is also oriented such that rear side 301 of shoe 120 is facing toward the rear side 302 of receptacle 211. In some embodiments, shoe 120 in receptacle 211 is shaped such that shoe 120 can only be inserted into receptacle 211 in a single orientation. In other embodiments, shoe 120 can be inserted within receptacle 211 in multiple orientations, but can only be fully engaged (as shown in FIG. 16) if shoe 120 and receptacle 211 are properly oriented.

Once properly oriented, controller 102 is moved toward patch 104 in the direction of arrow A1, such that shoe 120 enters receptacle 211 as shown in FIG. 15. Controller 102 is then advanced in the direction of arrow A2. This movement of controller 102 causes shoe 120 to engage with controller 102 as shown in FIG. 16. In particular, electrical circuitry 208 makes electrical contact with conductors of shoe 120 to electrically connect electrodes of patch 104 with electrical circuitry 208.

Electrical connectors are used to electrically connect conductors of shoe 120 with electrical circuitry 208. In one embodiment, male and female plug-type connectors are included as part of shoe 120 and electrical circuitry 208. In another embodiment, surface conductors are used to connect with protruding electrical contacts, such as used in Universal Serial Bus (USB) connectors and for connecting memory cards with memory slots. Other electrical connectors are used in other embodiments.

As described above, FIGS. 14-16 illustrate a two-step method of connecting patch 104 and controller 102. The first step involves moving controller 102 in the direction of arrow A1, and the second step involves moving controller 102 in the direction of arrow A2. This method of connection is partially a result of the "L-shape" of shoe 120. Shoe 120 has a first portion 304 that extends generally normal to a surface of insulating layer 212, and a second portion 306 that extends at generally a right-angle to the first portion 304.

One of the benefits of this shape of shoe 120 is that it resists unintentional disengagement of controller 102 from patch 104, once controller 102 is properly connected (as shown in FIG. 16). For example, if a force is applied to controller 102 in a direction opposite arrow A1, the second portion of shoe 120 resists disengagement of controller 102 from patch 104. Sideways forces (e.g., forces normal to arrow A1 and arrow A2) are also resisted, as well as a force in the direction of arrow A2. A force in the direction opposite arrow A2 will result in disconnection of shoe 120 from electrical circuitry 208. However, shoe 120 will still provide support to receptacle 211 unless controller 102 is arranged vertically below patch 104. This allows the user to manually grasp controller 102 before it becomes completely disconnected from patch 120 and reconnect controller 102, if desired. If controller 102 is arranged vertically below patch 104, then gravity will tend to pull controller 102 away from patch 104.

In another embodiment, shoe 120 has a generally linear shape (not shown in FIGS. 14-16), such that shoe 120 is plugged directly into controller 102 in a single step, namely the insertion of shoe 120 into receptacle 211. In this embodiment, electrical circuitry 208 includes an electrical connector that is in line with the path of entry of shoe 120 into receptacle 211 or directly surrounds the point of entry.

In another possible embodiment, shoe 120 has an "L-shape" but receptacle 211 is arranged on a side of controller 102. In this embodiment, connection of controller 102 with patch 104 is accomplished in a single step—insertion of a second portion of shoe 104 into the side receptacle.

Some embodiments of shoe 120 and receptacle 211 are arranged and configured to safely disconnect from each other upon the application of a sufficient force. If the user bumps device 100 on another object, for example, it is preferred that controller 102 electrically disconnects from patch 104 before patch 104 becomes disengaged from the patient. Shoe 120 and receptacle 211 are designed to remain connected unless a sufficient force is applied to controller 102 and before the force becomes large enough to disconnect patch 104 from the patient.

Figure 17:
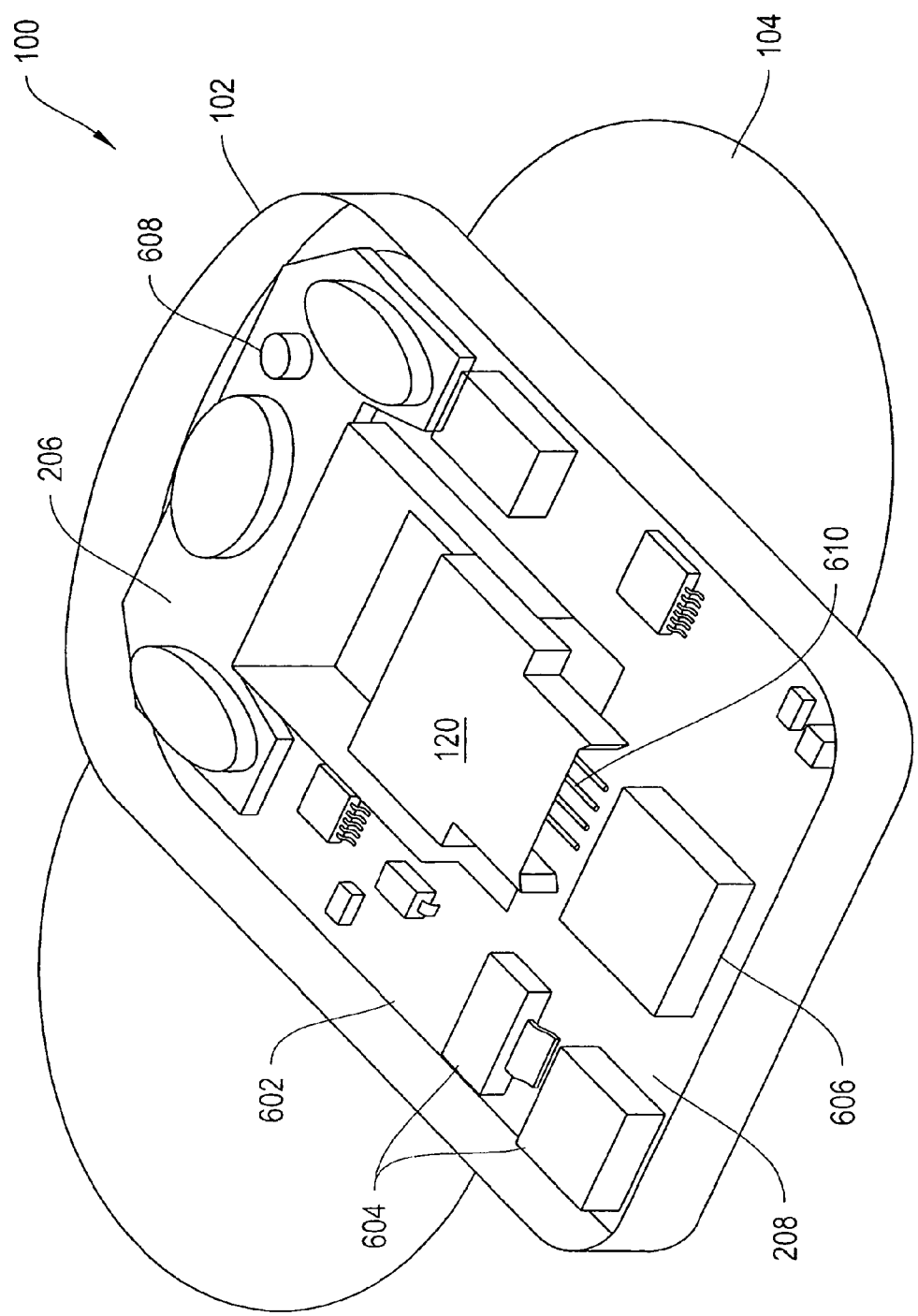
FIG. 17 is a perspective top view of the device shown in FIG. 12 in a partially assembled configuration.

FIG. 17 is a perspective top view of an exemplary embodiment of partially assembled device 100. In this figure, upper housing 202 and battery 204 (shown in FIG. 13) are removed. Device 100 includes controller 102 and patch 104. Controller 102 includes user input device 206 and electrical circuitry 208. Electrical circuitry 208 includes circuit board 602 and electronic components 604. Electrical components 604 include transformer 606, status indicator 608, and electrical connector 610.

In FIG. 17, shoe 120 is shown in the fully connected position, such as shown in FIG. 16. When in this position, electrical connectors of shoe 120 mate with electrical connectors 610 of electrical circuitry 208. Circuit board traces on or within circuit board 602 communicate electrical signals between electrical components 604 and shoe 120.

Some embodiments of electrical circuitry 208 include transformer 606. In some embodiments (such as shown in FIG. 13), the transformer is mounted on a surface of the circuit board. To reduce space consumed by transformer 606, some embodiments include a hole in circuit board 602. Transformer 606 is inserted within the hole to reduce the overall distance that transformer 606 extends above circuit board 602. This allows upper and lower housing 202 and 210 to have a reduced profile. Some embodiments include a receptacle in the circuit board (e.g., circuit board 29 of FIG. 5) to accept a component such as portion 42 of shoe 13. This allows the allows pins 31 of circuit board 29 to extend into the space created by connector receptacle 24.

Some embodiments include one or more status indicators 608. Status indicators inform a user of the operational status of device 100 and can come in the form of visual, audible, and/or tactile indicators. Examples of suitable status indicators 608 include a light, an LED, a liquid crystal or other type of display, a speaker, a buzzer, and a vibrator. Status indicators 608 are used in some embodiments to show whether device 100 is ON or OFF. In other embodiments, status indicators 608 communicate an operational mode, such as a type of therapy being provided, or a change in operational mode, such as an increase or decrease in amplitude. In yet other embodiments, status indicators 608 are used to show battery power status (e.g., full power, percentage of full power, or low on power/in need of charge), or charging status (e.g., charging or fully charged). Other indicators are used in other possible embodiments. Speakers, buzzers, and vibrators are particularly useful for those with certain disabilities or impairments and also for communication when the device is located in an area that is not easily visible (e.g., on the back of a patient).

Figure 18:
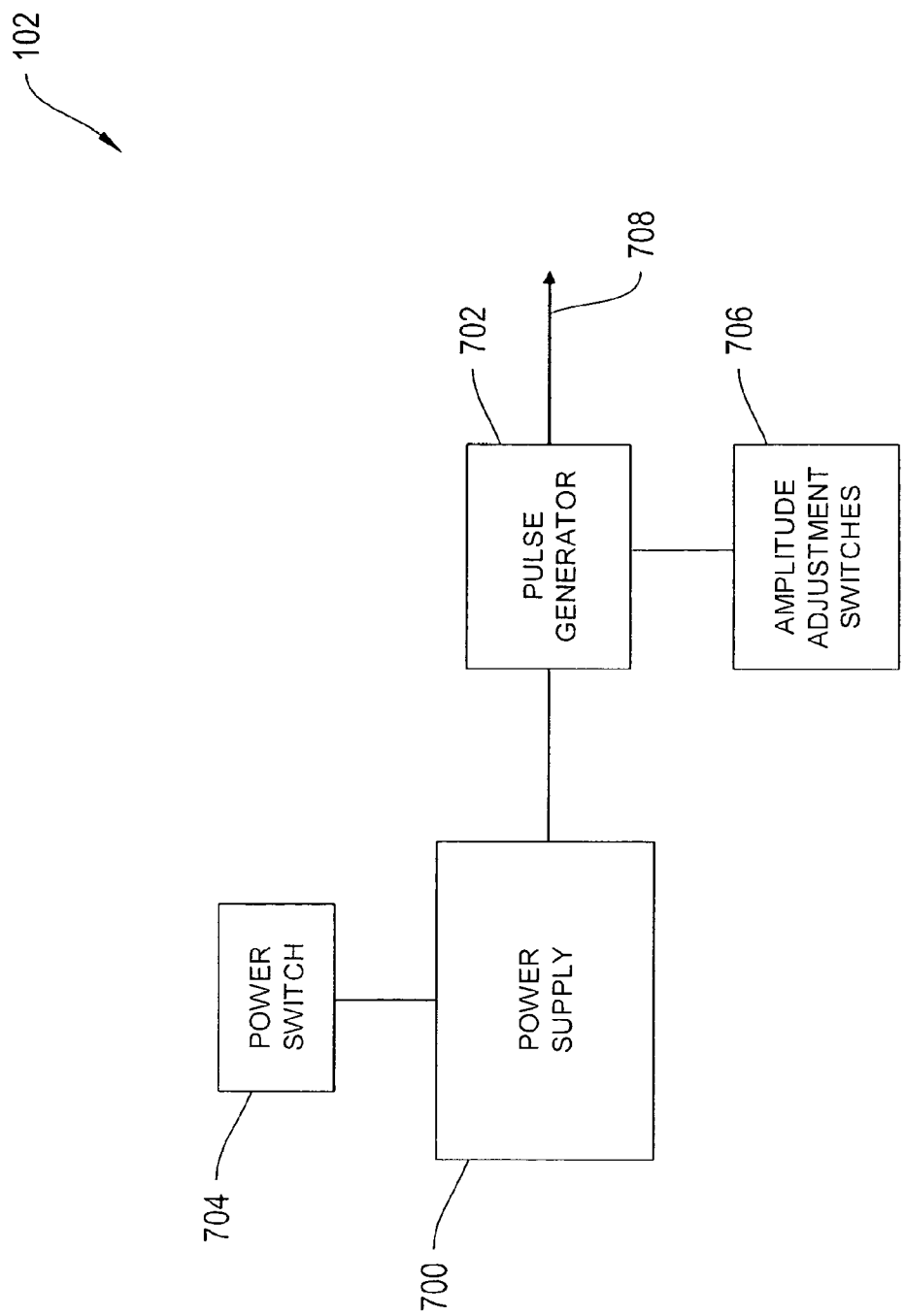
FIG. 18 is a block diagram of an electrical schematic for the controller shown in FIG. 14.

FIG. 18 is a block diagram of an exemplary electrical schematic for controller 102. Controller 102 includes power supply 700, pulse generator 702, power switch 704, amplitude adjustment switches 706, and output 708.

Power supply 700 provides electrical power to controller 102. In some embodiments, power supply 700 includes a battery and also includes power filtering and/or voltage adjustment circuitry. Power supply 700 is electrically coupled to power switch 704 and to pulse generator 702. Power switch 704 receives input from a user through power button 110 (e.g., shown in FIG. 12) and operates with power supply 700 to turn controller 102 ON or OFF.

Pulse generator 702 generates therapeutic electrical signals. Pulse generator 702 is electrically coupled to output 708 and provides the electrical signals to output 708. In turn, output 708 is electrically coupled to patch electrodes to deliver the electrical signals to the therapeutic location of the patient. Amplitude adjustment switches 706 are electrically coupled to pulse generator 702 and receive input from the user through amplitude adjustment buttons 112 and 114 (e.g., shown in FIG. 12). Amplitude adjustment switches 706 operate with pulse generator 702 to adjust the intensity of the electrical signals sent to output 708.

Some examples of suitable pulse generators are described in U.S. Pat. Nos. 4,887,603 and 4,922,908, both by Morawetz et al. and titled MEDICAL STIMULATOR WITH STIMULATION SIGNAL CHARACTERISTICS MODULATED AS A FUNCTION OF STIMULATION SIGNAL FREQUENCY, the disclosure of which is hereby incorporated by reference in its entirety. In some embodiments, the electrical signals generated by pulse generator 702 are simple modulated pulse (SMP) signals. Other configurations and electrical signals are possible.

Figure 19:
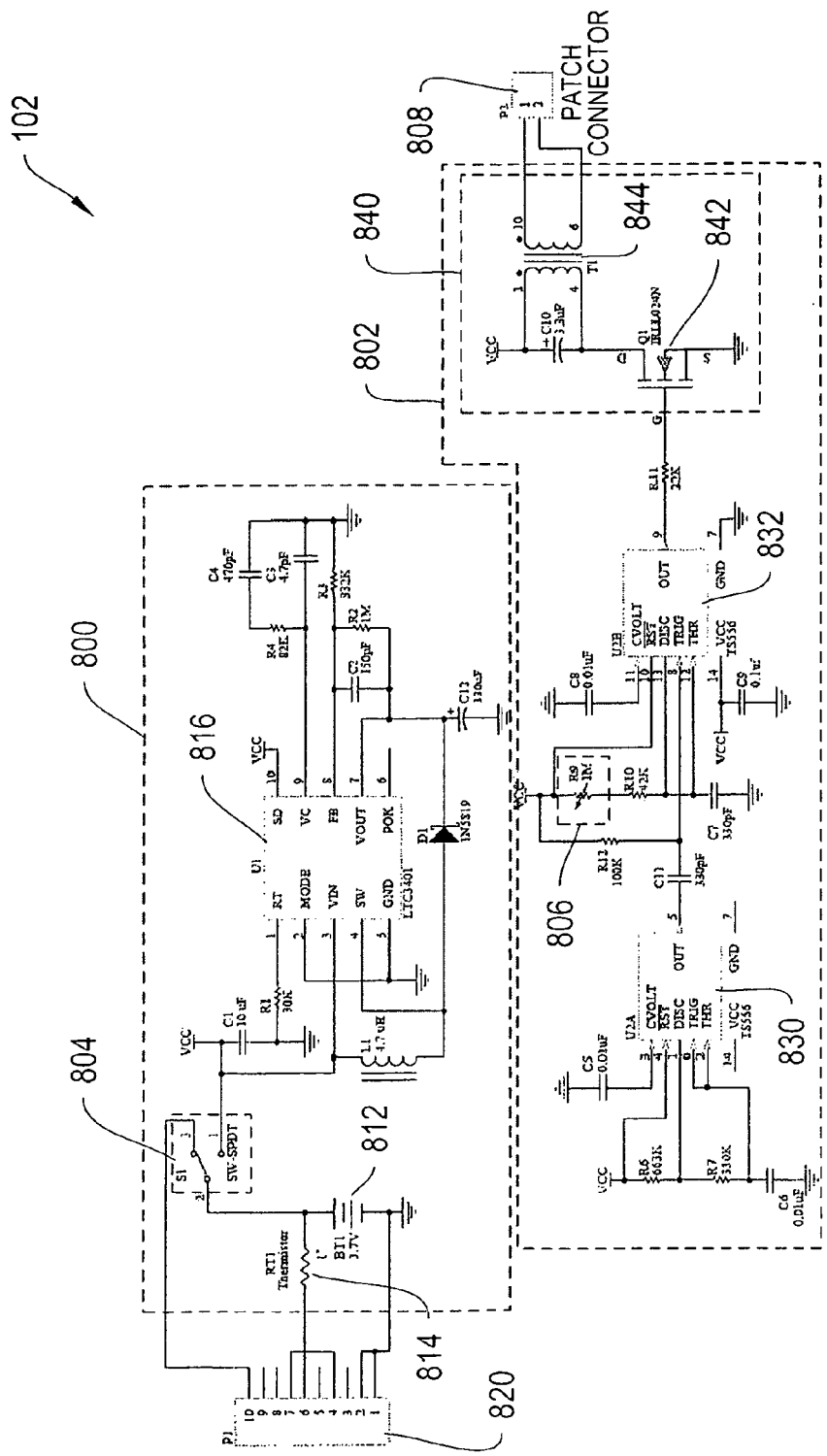
FIG. 19 is an electrical schematic of an exemplary circuit for the controller shown in FIG. 14.

FIG. 19 is an electrical schematic of an exemplary circuit for controller 102. Controller 102 includes power supply 800, pulse generator 802, power switch 804, amplitude adjustment switch 806, and output 808. Power supply 800 includes battery 812, thermistor 814, step up converter 816, and other electrical components. Power supply 800 is electrically coupled to supply power to pulse generator 802. In addition, power supply 804 is electrically coupled to connector block 820 that is used to supply power to power supply 800 to charge battery 812.

In this example, battery 812 is a lithium-ion battery having a voltage of about 3.7 to 4.2 volts, although other battery types and voltages are used in other embodiments. Thermistor 814 is electrically coupled between battery 812 and connector block 820 and is used to detect the temperature of battery 812 to ensure that battery 812 is not overheated while recharging. Power switch 804 is used to turn controller 102 ON or OFF. Power switch 804 may be easily controlled, for example, by user control 110. In one embodiment, switch 804 is a single pole double throw (SPDT) switch, as shown. Power supply 800 also includes step up converter 816. Step up converter 816 operates to increase the voltage of power from battery 812 to a desired voltage. One suitable step up converter is the LTC3401 micropower synchronous boost converter that is distributed by Linear Technology Corporation, with headquarters in Milpitas, Calif.

Pulse generator 802 receives power from power supply 700 and generates a therapeutic electrical signal. The therapeutic electrical signal is provided by pulse generator 802 to output 808. Pulse generator 802 includes amplitude adjustment switch 806. Amplitude adjustment switch 806 may be easily controlled, for example, by user controls 112 and 114. In this embodiment, amplitude adjustment switch 806 is a potentiometer. When the potentiometer is adjusted, intensity of the electrical signal generated by pulse generator 802 is increased or decreased accordingly.

In this example, pulse generator 802 includes first and second timers 830 and 832 as well as additional circuitry as shown. In one embodiment, both timers 830 and 832 are the TS556 low-power dual CMOS timer, distributed by STMicroelectronics, with headquarters in Geneva, Switzerland.

Pulse generator 802 also includes output stage 840. Output stage 840 includes MOSFET 842 and transformer 844. Output stage 840 acts to increase the output voltage of the electrical signal before sending the electrical signal to output 808.

Figure 20:
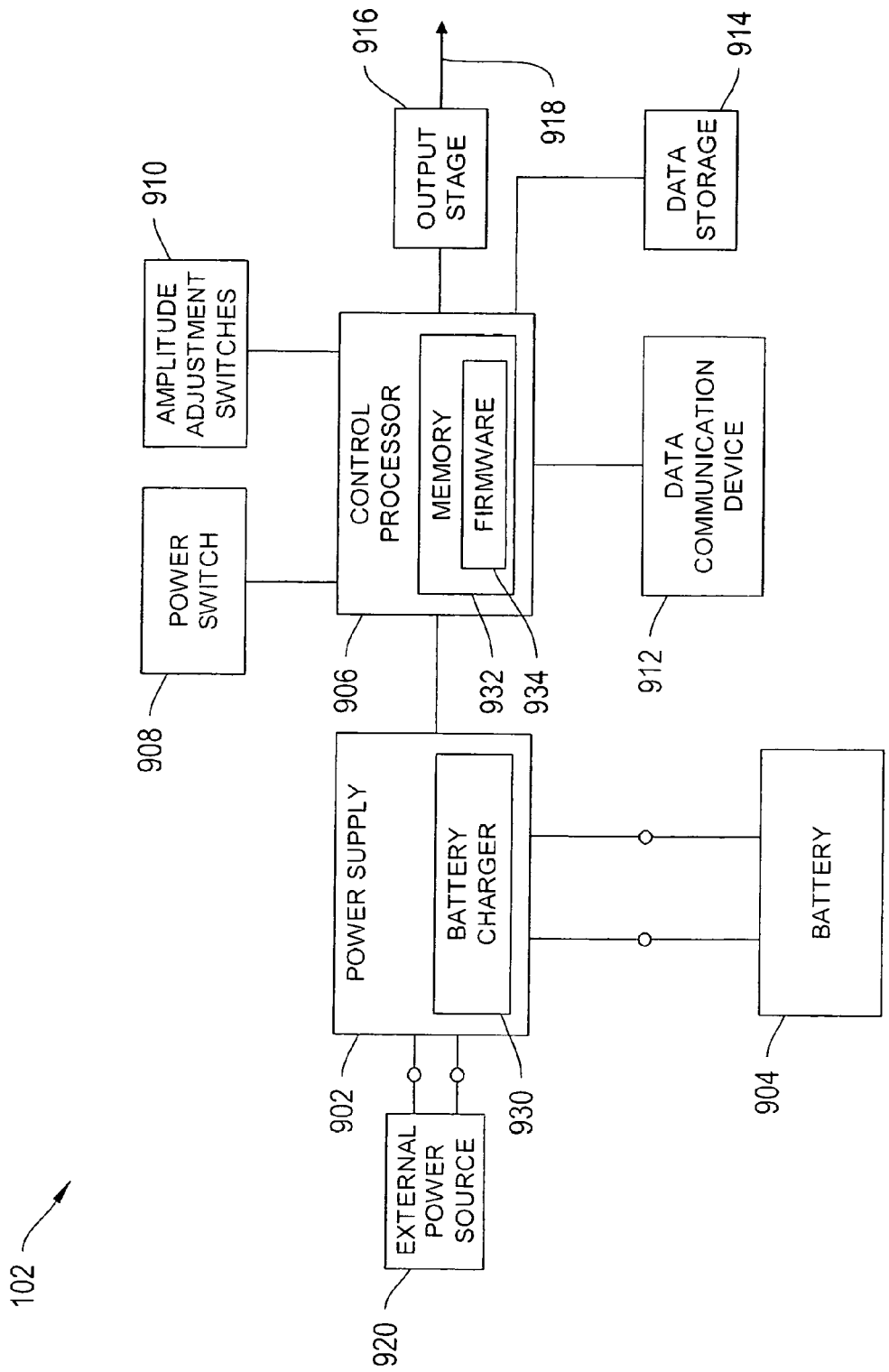
FIG. 20 is another block diagram of an electrical schematic for the controller shown in FIG. 14.

FIG. 20 is a block diagram of another exemplary electrical schematic for controller 102. In this embodiment, controller 102 is formed from primarily digital circuitry. Controller 102 includes power supply 902, battery 904, controller processor 906, power switch 108, amplitude adjustment switches 910, data communication device 912, data storage device 914, output stage 916, and output 918. Controller 102 is connected to external power source 920, to charge battery 904. In one embodiment, external power source 920 is a home or commercial power supply, such as available through an electrical power outlet. In another embodiment, external power source 920 is an vehicle power supply, such as accessible through a 12V receptacle.

During normal operation, power supply 902 receives power from battery 904. Power supply 902 converts the battery power to a desired voltage before supplying the power to other components of controller 102. Power supply 902 also includes battery charger 930. Battery charger 930 receives power from an external power supply and operates to recharge battery 904.

Control processor 906 controls the operation of controller 102. Control processor 906 is powered by power supply 902. Control processor 906 also generates electrical signals that are provided to output stage 916.

Control processor 906 is electrically coupled to power switch 908 and amplitude adjustment switches 910. Control processor 906 monitors the state of power switch 908. When control processor 906 detects that the state of power switch 908 has changed, control processor 906 turns controller 102 ON or OFF accordingly. Control processor 906 also monitors the state of amplitude adjustment switches 910. When control processor 906 detects that the state of amplitude adjustment switches 910 has changed, control processor 906 increases or decreases the intensity of electrical signals provided to output stage 916 accordingly.

Control processor 906 includes memory 932. Firmware 934 is stored in memory 932. Firmware 934 includes software commands and algorithms that are executed by control processor 906 and defines logical operations performed by control processor 906. The software commands and algorithms in firmware 932 may be used to operate the electrical stimulation device in a desired mode, such as a mode that provides transcutaneous electrical nerve stimulation therapy. In certain embodiments, controller 102 includes a data communication device 912. Data communication devices include wired or wireless communication devices, such as serial bus communication devices (e.g., a Universal Serial Bus communication devices), local area networking communication devices (e.g., an Ethernet communication device), a modem, a wireless area networking communication device (e.g., an 802.11x communication device), a wireless personal area networking device (e.g., a Bluetooth™ communication device), or other communication device.

Data communication device 912 can be used to send and receive data with another device. For example, data communication device 912 can be used to download different firmware 934 to the controller 102 to alter the operation of control processor 906, and operate the therapeutic electrical stimulation device in a desired mode, such as a mode that provides iontophoresis therapy. In certain embodiments, a firmware algorithm must be purchased before it can be downloaded by a user. In certain embodiments, the a user must access a patient interface of a web server or other similar interface before downloading a firmware algorithm. Data communication device 912 can also be used to upload data to another device. For example, control processor 906 stores a therapy log in data storage device 914. The control processor 906 can be used to upload the therapy log to an external device by sending the data log to data communication device 912.

Data storage device is a device capable of storing data, such as a memory card or other known data storage device. In some embodiments, data storage device 914 is part of memory 932.

When controller 102 is ON, control processor 906 generates therapeutic electrical signals, and provides those signals to output stage 916. Output stage 916 converts and filters the electrical signals, and then provides the electrical signals to output 918. Output 918 is electrically coupled to a patch that delivers electrical signals to the patient.

Figure 21:
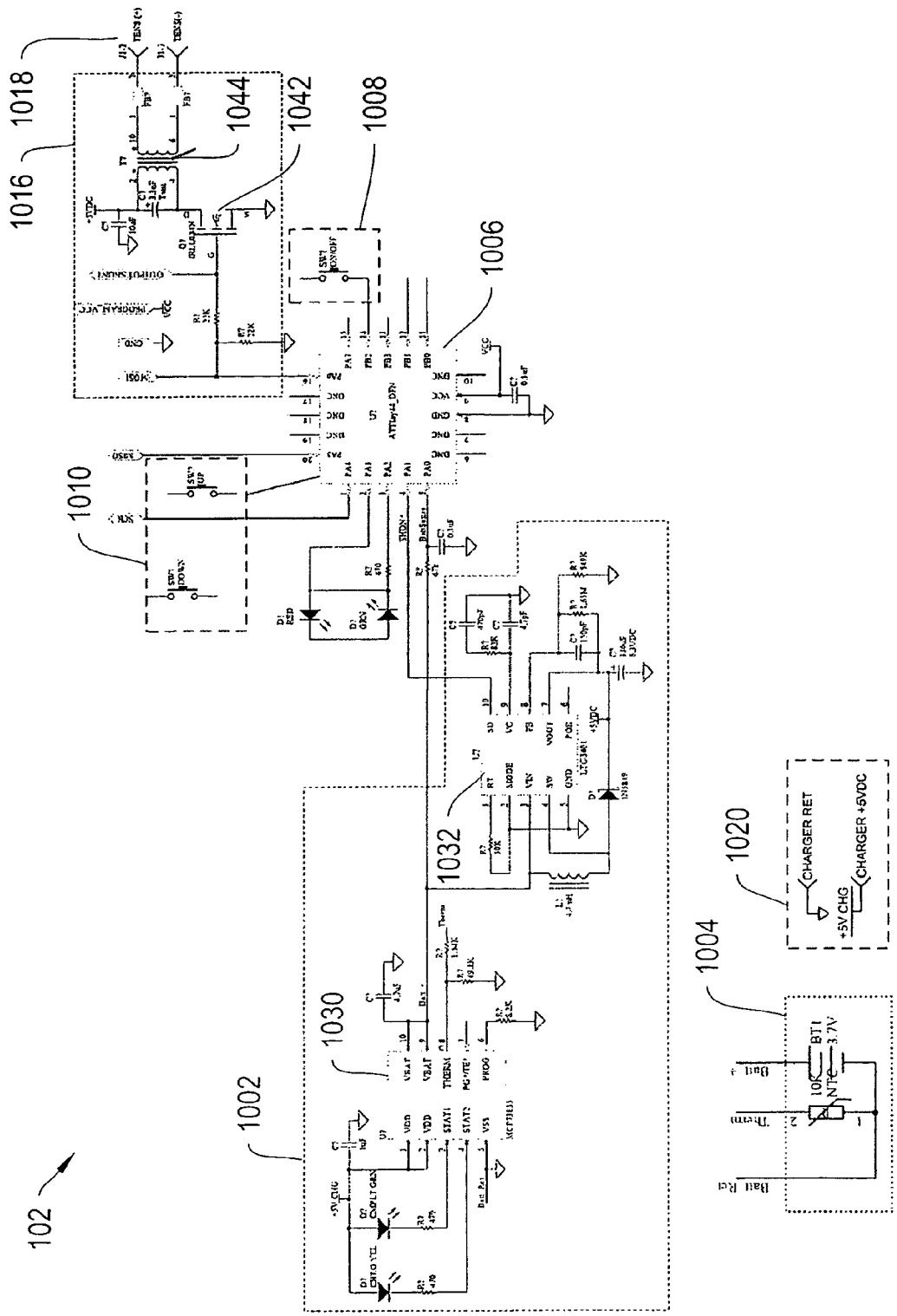
FIG. 21 is another electrical schematic of an exemplary circuit for the controller shown in FIG. 14.

FIG. 21 is an electrical schematic of another exemplary circuit for controller 102. In this embodiment, controller 102 includes a control processor 1006 that controls the operation of controller 102. In this embodiment, controller 102 is made from primarily digital circuitry. Controller 102 includes power supply 1002, battery 1004, control processor 1006, power switch 1008, amplitude adjustment switches 1010, output stage 1016, and output 1018. Controller 102 can also be connected to external power source 1020, such as to charge battery 1004.

In this embodiment, power supply 1002 includes a lithium-ion charge management controller 1030 and a step up converter 1032, as well as other electrical components as shown. An example of a suitable lithium-ion charge management controller 1030 is the MCP73833 stand-alone linear lithium-ion charge management controller manufactured by Microchip Technology Inc., of Chandler, Ariz. An example of a suitable step up converter is the LTC3401 micropower synchronous boost converter.

Battery 1004 provides power to power supply 1002. In this example, battery 1004 is a lithium-ion 3.7V battery. Power supply 1002 can also be connected to external power source 1020, such as a 5V DC power source. External power source 1020 provides power to power supply 1002 that enables power supply 1002 to recharge battery 1004. In some embodiments, battery 1004 includes a thermistor to monitor the temperature of battery 1004 during charging.

Control processor 1006 controls the operation of controller 102. One example of a suitable control processor 1006 is the ATtiny44 8-bit microcontroller manufactured by Amtel Corporation, located in San Jose, Calif. Alternatively, various other processing devices may also be used including other microprocessors, central processing units (CPUs), microcontrollers, programmable logic devices, field programmable gate arrays, digital signal processing (DSP) devices, and the like. Control processor 1006 may be of any general variety such as reduced instruction set computing (RISC) devices, complex instruction set computing devices (CISC), or specially designed processing devices such as an application-specific integrated circuit (ASIC) device.

Control processor 1006 is electrically coupled to power switch 1008 and amplitude adjustment switches 1010. Power switch 1008 provides signals to control processor 1006 that cause control processor 1006 to alternate controller 102 between ON and OFF states accordingly. Amplitude adjustment switches 1010 instruct control processor 1006 to adjust the intensity of the electrical signals generated by controller 102. Electrical signals generated by control processor 1006 are passed to output stage 1016.

Output stage 1016 converts the electrical signals received from control processor 1006 to an appropriate form and then provides the electrical signals to output 1018. In this example, output stage 1016 includes MOSFET 1042 and transformer 1044. Other embodiments do not include transformer 1044, but rather use a flyback converter or other converter to generate an appropriate output signal.

Figure 22:
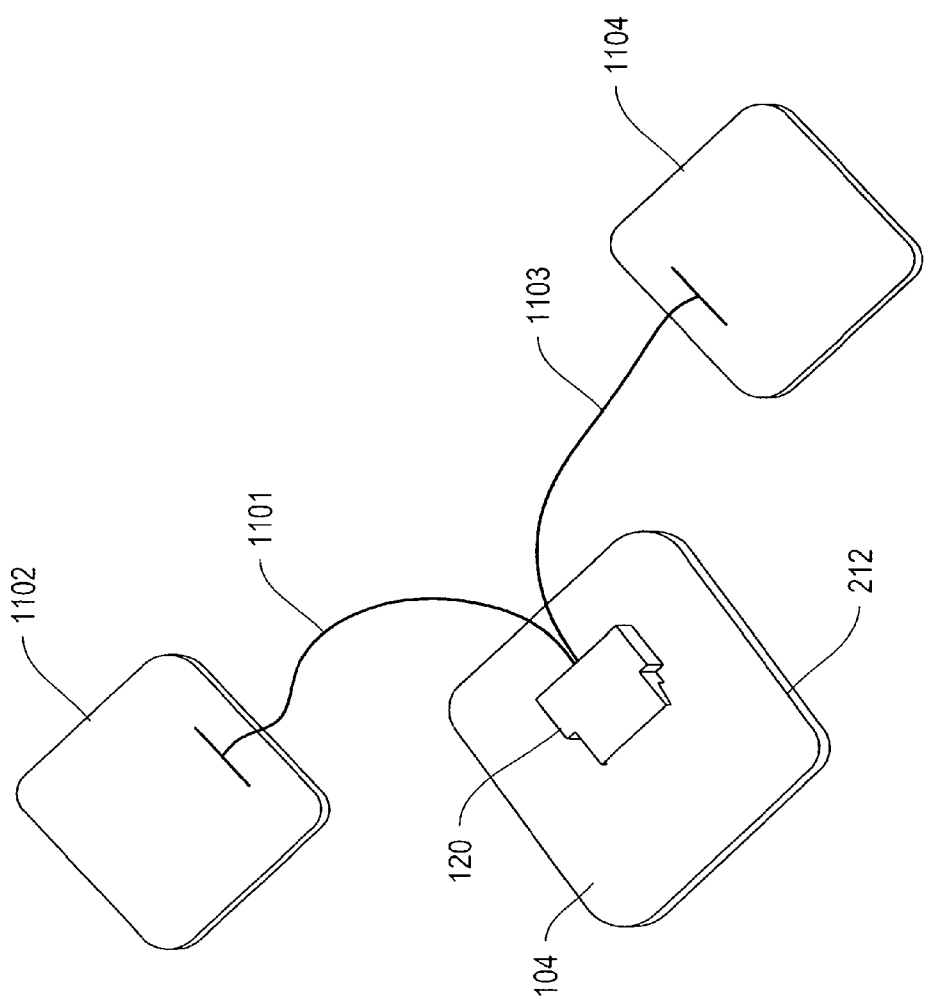
FIG. 22 is a top perspective view of another embodiment of a patch.

FIG. 22 is a top perspective view of another exemplary embodiment of patch 104. Patch 104 includes insulating layer 212 and shoe 120. Shoe 120 is connected to a surface of insulating layer 212. In this embodiment, shoe 120 includes wires 1101 and 1103 that are electrically coupled to conductors within shoe 120. The wires 1101 and 1103 may be connected to conductors within shoe 120 using a metal crimp or other suitable method of electrical connection. Wires 1101 and 1103 are also connected at an opposite end to patches 1102 and 1104. Patches 1102 and 1104 may include electrodes such as a conducting polymer material. Patch 104 may be used in a garment or medical device such as the belt depicted in FIGS. 23 A-D.

In one embodiment, patch 104 includes one or more electrodes, such as shown in FIG. 13, and an adhesive layer that allows patch 104 to be connected to a patient or other device. In another embodiment, patch 104 does not include an electrode, but rather passes electrical signals through wires 1101 and 1103 to separate patches 1102 and 1104. Patches 1102 and 1104 include an insulating layer and one or more electrodes, but do not include a shoe. Instead, patches 1102 and 1104 receive electrical signals from the shoe included in patch 104. Patches 1102 and 1104 can be adhered to the patient such as with an adhesive layer. The electrodes of patches 1102 and 1104 direct the electrical signals to desired therapeutic locations of the patient.

Other embodiments include any number of wires 1101 and 1103 and any number of patches 1102 and 1104 (e.g., one patch, two patches, three patches, four patches, five patches, etc.) as desired for a particular therapy. Shoe 120 includes an appropriate number of electrical conductors that can provide multiple electrical conduction channels for communicating electrical signals between controller 102 (such as shown in FIG. 12) and the patches. In some embodiments, wires 1101 and 1103 are formed adjacent to or within insulating layers to provide additional protection to the wires from damage. In some embodiments, wires 1101 and 1103 are other types of electrical conductors. In other examples, multiple electrode sites can be positioned in a patch 104. For example, a quad-patch can be formed with an insulating layer having four lobes, with each lobe having an electrode for delivery of therapy, as described below with respect to FIG. 23D. Other configurations are possible.

In some embodiments, patches 104, 1102, and 1104 are held in place by a band, strap, brace, built, garment, active wear, or other suitable supporting object. For example, patches can be formed integral with a supporting object or inserted within a pocket or recess of a supporting object. Some embodiments include integrated hot or cold packs. The connection to a supporting object may be made by stitching, gluing, snapping, velcroing, embedding in a laminate layer or any other possible way to connect one or more of elements 1101, 1103, 104, 1102 and 1104 to a supporting material. In embodiments where one or more of elements 1101, 1103, 104, 1102 and 1104 are formed integral with a supporting object, they may be washed or cleaned (e.g., in a washing machine, soap and water, dry cleaned, etc.) along with the supporting object. Some further examples are illustrated in FIG. 23A.

Figure 23A:
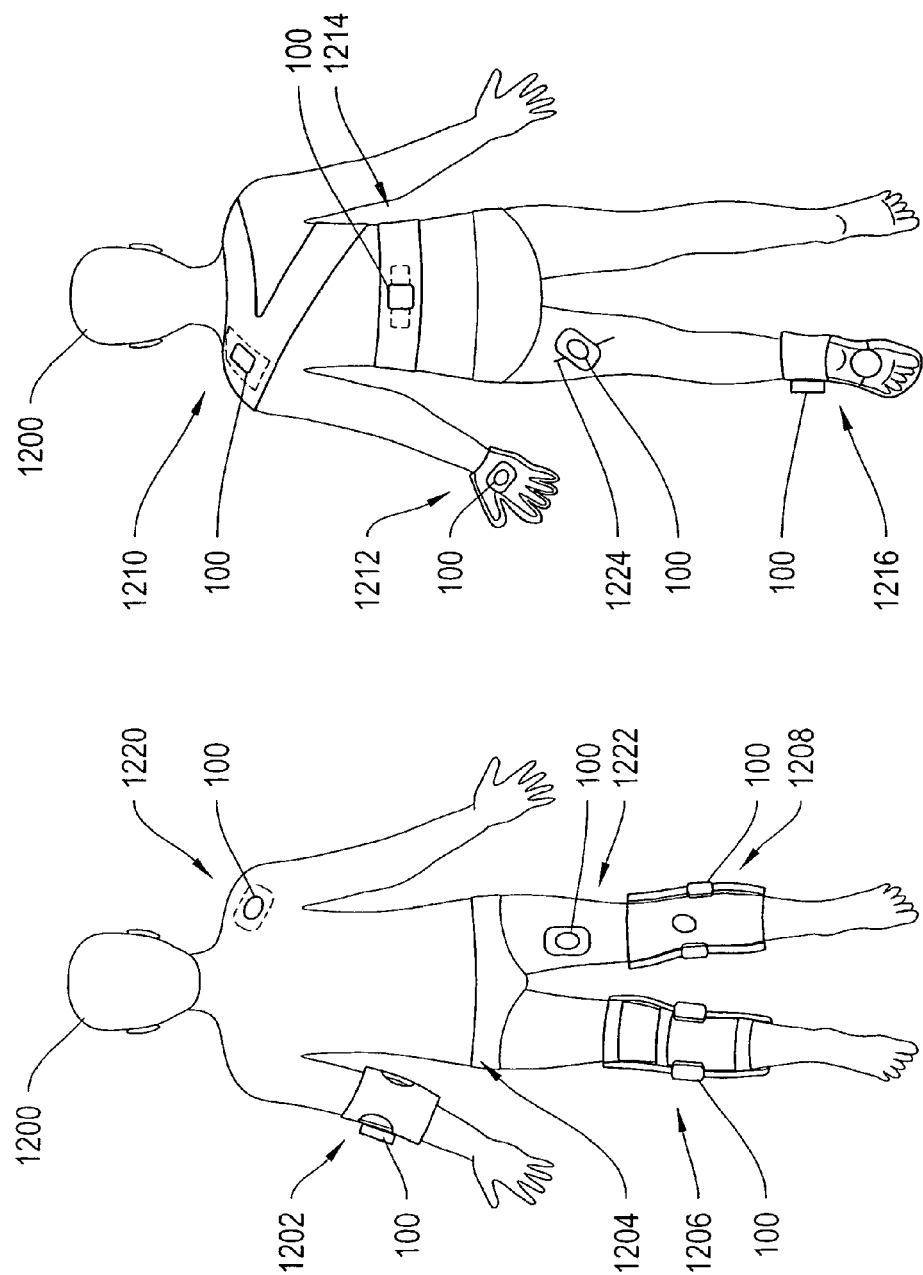
FIG. 23A is a schematic illustration of possible applications and configurations for the device shown in FIG. 12 and FIG. 1.

FIG. 23A schematically illustrates some of the possible applications and configurations of therapeutic electrical stimulation device 100. FIG. 23A illustrates a patient 1200 including a front profile (left) and a rear profile (right).

One application of device 100 is to reduce joint pain or to reduce swelling in a joint. For example, device 100 is integrated into elbow brace 1202, hip support 1204, knee braces 1206 and 1208, shoulder brace 1210, glove 1212, back support 1214, and sock 1216 to provide relief from pain or swelling at the respective location. This illustrates that device 100 can be used to treat symptoms at the patient's elbow, hip, knee, shoulder, wrist, hand, fingers, back, ankle, foot, or any other joint in the body.

Alternatively, embodiments of device 100 are directly adhered to the desired therapeutic location, such as shoulder 1220, as described herein.

Another application of device 100 is to reduce muscle or other tissue pain at any desired therapeutic location on the body. For example, device 100 is adhered to thigh 1222 of patient 1200.

Another application of device 100 is to stimulate wound healing. For example, device 100 can be placed on or adjacent to wound 1224 (shown on the rear left thigh of patient 1200). Some embodiments of device 100 act as electronic adhesive bandage to promote wound healing and reduce pain associated with wound 1224. Some embodiments of device 100 include controller 102 and patch 104 (such as shown in FIG. 12) as a single non-separable unit.

Furthermore, alternate patch configurations (such as shown in FIG. 22) can be used to supply therapeutic electrical signals to multiple locations of the body (e.g., a back and hip) or to multiple regions of the same body part (e.g., opposite sides of the knee or top and bottom of the foot).

Figure 23C:
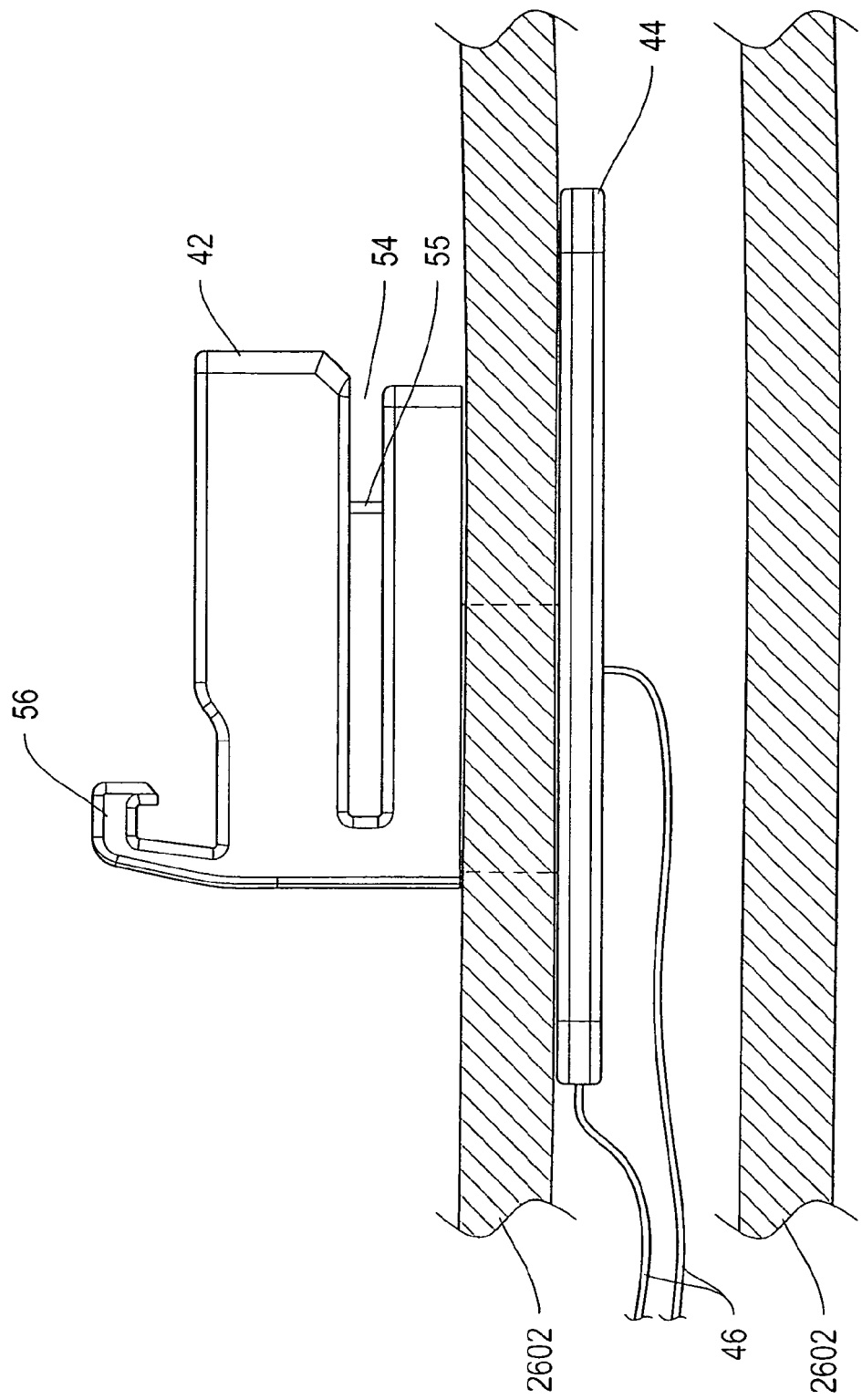
FIG. 23C is a side cross sectional view of a possible configuration for the devices shown in FIG. 23A.

FIGS. 23B and 23C show an example of how a therapeutic stimulation device, such as device 100, may be configured to provide therapy to as user (e.g., as depicted in FIG. 23A). In FIG. 23B, shoe 13 is attached to a garment 2602. The shoe 13 may be attached to garment 2062 in a variety of ways, for example it may be stitched or glued to the garment or embedded in a laminate layer.

The garment 2062 may be any type of garment or medical device such as clothing or elbow brace 1202, hip support 1204, knee braces 1206 and 1208, shoulder brace 1210, glove 1212, back support 1214, and sock 1216. The garment 2602 is connected to one or more electrodes 1502 positioned adjacent the garment and electrically connected to lead wire 46. One or more electrodes 1502 may be placed in various positions on the garment 2602 (e.g., the layout shown in FIG. 23D). The electrodes 1502 may be wired and connected electrically in various patterns and orders and to one or more different shoes 13. For example, two of the electrodes 1502 (right) of FIG. 23D are electrically connected to each other but not to the electrodes 1502 (left). The variance in electrode patterns and electrical connections allows for the ability to create various stimulation schemes for therapy. The electrodes are made of a conductive polymer, stainless steel or other suitable material, and may be integrated within the garment or connected to the outside of the garment by sewing, gluing, velcroing or other suitable attachment schemes.

In certain embodiments, stainless steel snaps (male connector) are stamped through the garment and are thereby securely connected to the garment. The snaps are electrically conductive and allow for an electrode (female connector) to mechanically and electrically connect to the male snaps and become secured to the garment. The male snaps are connected to leads wires 46 and 48, which are electrically connected to the shoe 13. Snap connectors for electrodes are described in more detail in U.S. Pat. No. 6,438,428 which is incorporated herein by reference.

As shown in FIGS. 23B and 23C, the base 44 of shoe 13 and one or more of the lead wires 46 are positioned between layers of the garment 2602. This allows the wires 46 to be hidden and shielded from the user. The base 44 physically holds the shoe 13 within the garment to create a connection between the garment and the shoe. The top of shoe 13 is exposed on the outside of garment 2602, to allow connection to controller 11. In certain embodiments, shoe 13, lead wires 46, and electrode 1502 remain attached as a unit, while the controller 11 may be frequently detached and reused for other applications with other shoes or at a different times with the same shoe. In this example, the shoe 13, lead wires 46, and electrode 1502 elements may all be washed or cleaned together. Typically, the garment including the shoe, wire, and electrodes are used for about 6 months before being disposed and replaced.

In certain embodiments, the electrode 1502 connects directly to a user 1506 by sitting directly on top of the skin. In other embodiments, an adhesive layer 1504 is affixed to electrode 1502 and the adhesive layer affixes the electrode to the patient. The adhesive layer 1504 is a conductor to allow current to pass from the electrode 1502 to the patient 1506. The adhesive layer 1504 may be sticky on both sides so that a more reliable electrical and mechanical connection is made with the skin of a user. In certain embodiments only one side of the adhesive layer 1504 is sticky, and one side (e.g., the exposed side) of the electrode 1502 is sticky. Typically the adhesive layer 1504 is used only once before being disposed, though it may be reused multiple times.

In some embodiments, multiple devices 100 are in data communication with each other to synchronize therapies provided by each respective device. For example, wireless communication devices (e.g., 912 shown in FIG. 20) are used to communicate between two or more devices 100.

In some embodiments, device 100 is configured to provide interferential therapy, such as to treat pain originating within tissues deeper within the body than a typical TENS device.

Some embodiments of device 100 are configured for drug delivery. Such embodiments typically include a drug reservoir (such as absorbent pads) within patch 104 (e.g., shown in FIG. 13). Iontophoresis is then used to propel the drug (such as medication or bioactive-agents) transdermally by repulsive electromotive forces generated by controller 102. An example of a suitable device for iontophoresis is described in U.S. Pat. No. 6,167,302 by Philippe Millot, titled DEVICE FOR TRANSCUTANEOUS ADMINISTRATION OF MEDICATIONS USING IONTOPHORESIS, the disclosure of which is hereby incorporated by reference in its entirety.

Other therapies can also be delivered. For example, controller 100 can be programmed to deliver microcurrent. Such microcurrent can be a constant voltage that is delivered for wound healing purposes. Other therapies can be delivered to address pain, edema, drop-foot, and other abnormalities.

The components of the therapeutic electrical stimulation devices, such as device 10 and garment 2602, are manufactured to be disposable and replaced after the useful life of such components has expired. Useful life of a component can be defined, for example, by number of uses of the particular component, the lifetime of a component before wearing out, time established by the manufacturer, time available between reimbursements by Medicare or Medicaid (or other similar programs), or other similar standards. In certain embodiments, the controller is provided with a manufacturer-imposed useful life of about 5 years, such that upon the expiration of such 5 years, a replacement controller is made available to the patient. During its useful life, the controller may be reused for multiple applications on various different garments and with several different shoes 13. In certain embodiments, the garment, such as shown in FIG. 23A-D, including shoe 13 and patch 104, is provided with a manufacturer imposed useful life of about 6 months or less. In certain embodiments, the adhesive layer (e.g. adhesive layer 128) is provided with manufacturer imposed useful life of one application or use, though it may be reused multiple times. In certain embodiments, a user uses a certain number of adhesives (e.g., a package of 10) on a monthly basis.

In certain embodiments, the useful life of the component is predetermined prior to initial use or sale of the component, and it is replaced upon expiration of the useful life. In some implementations, the predetermined useful life coincides with a period established by regulatory or other administrative authority by paying for or reimbursing for such component. In some embodiments, such predetermined useful life is shorter than the period in which the component becomes physically worn out or inoperable.

Figure 24:
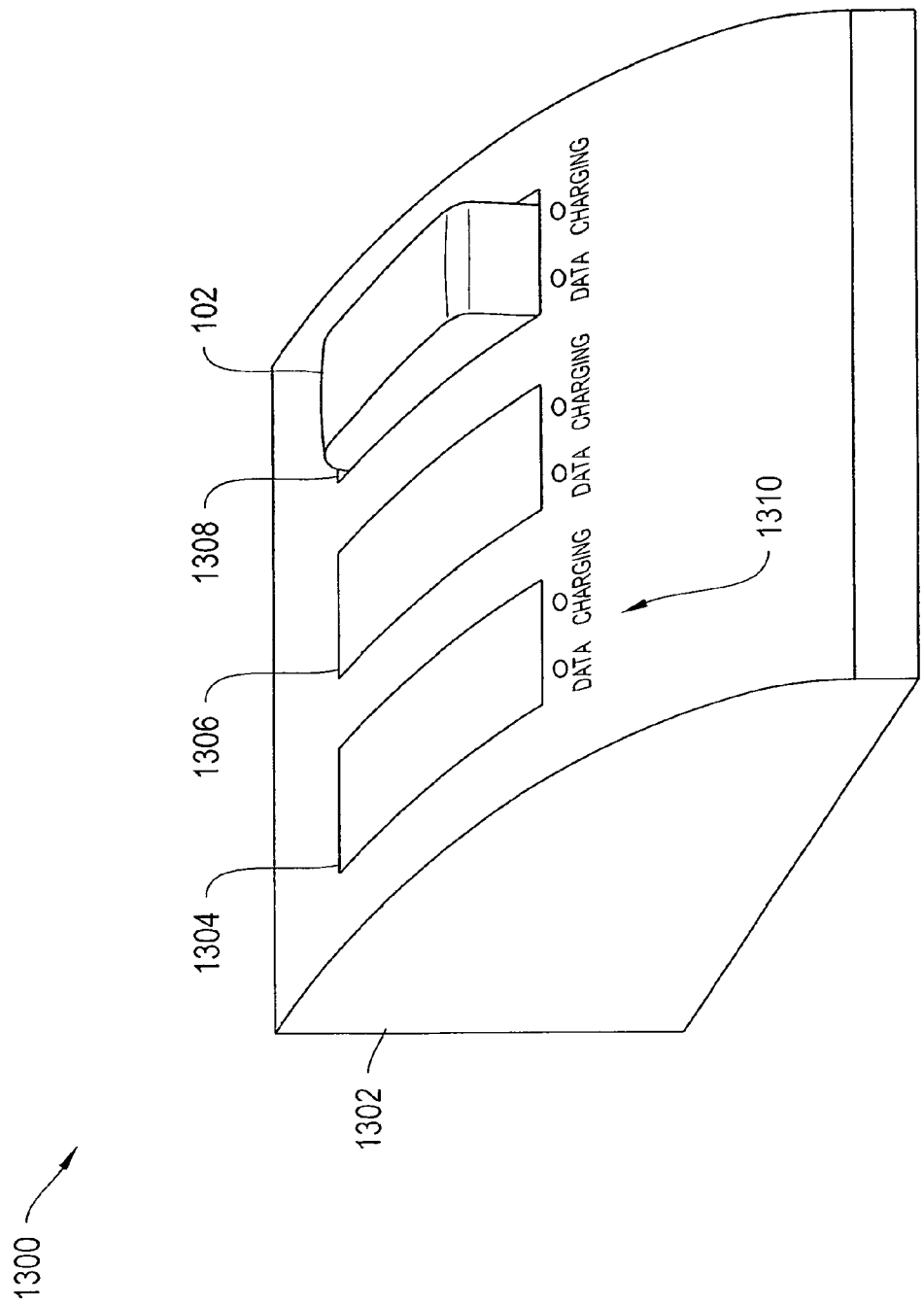
FIG. 24 is a perspective view of an exemplary docking station.

FIG. 24 is a perspective view of an exemplary docking station 1300. Docking station 1300 includes housing 1302 including multiple slots 1304, 1306, and 1308 and status indicators 1310 associated with each slot.

Each slot of the docking station 1300 is arranged and configured to receive a controller 102 of a therapeutic electrical stimulation device 100, such that multiple controllers 102 can be connected with docking station 1300 at any time. However, some embodiments of docking station 1300 include only a single slot 1304 or other port for connection to a single controller 102. Other embodiments include any number of slots as desired.

Figure 8B:
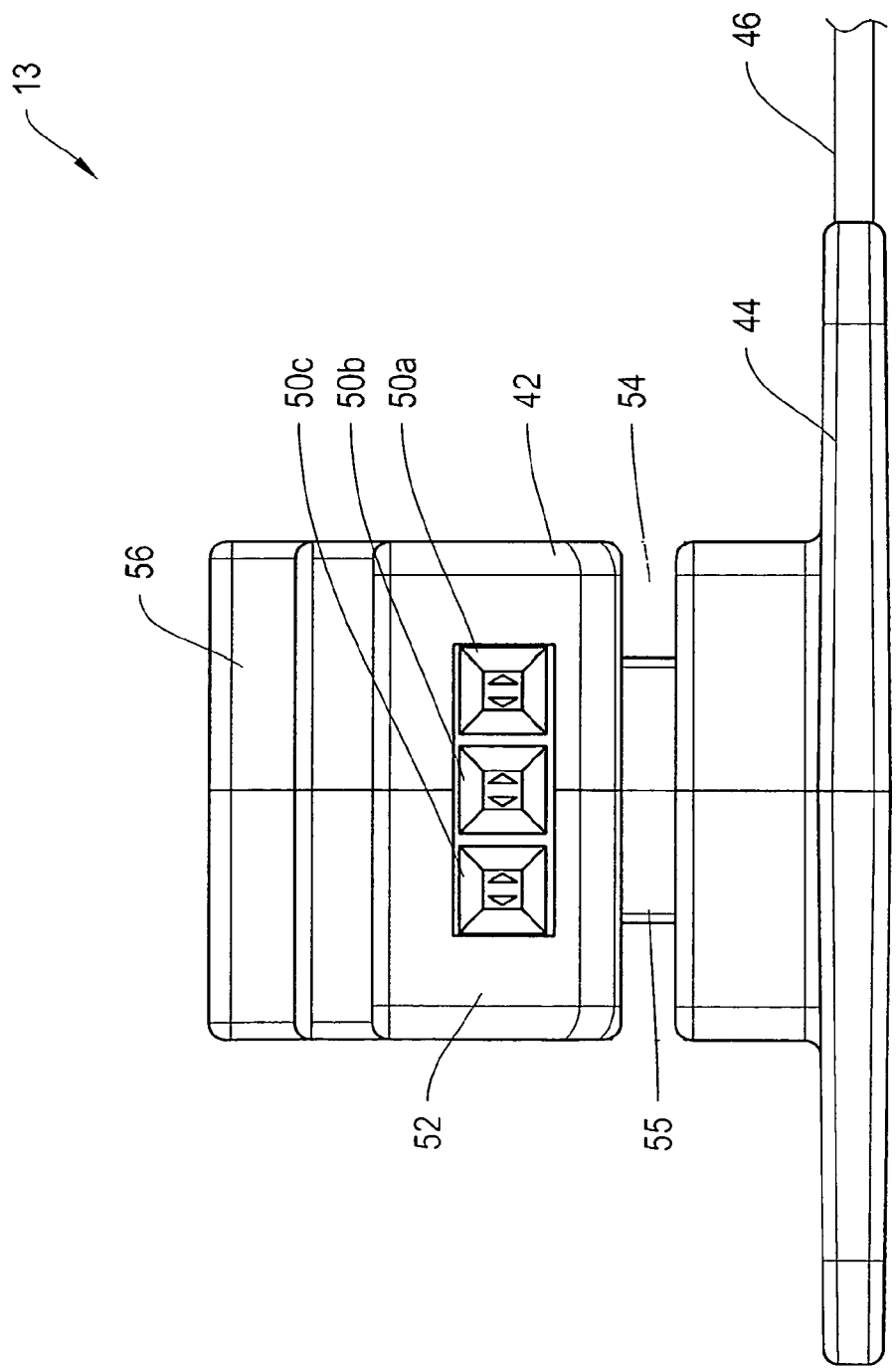
FIG. 8B is a front view of a shoe of the therapeutic electrical stimulation device shown in FIG. 1

Docking station 1300 includes an electrical connector similar to connector 51 in shoe 13, such as shown in FIGS. 8A and 8B. When device 100 is inserted into docking station 1300, shoe 120 engages with receptacle 211, such as described with respect to FIGS. 14-16. When the shoe 120 engages with receptacle 211, pins 31a-31c combine with receptacle 211 to form an electrical connection. When device 100 is coupled with docking station 1300, data is transferred through pin 31a to the docking station 1300 through an abutting connector wire inside the station 1300, similar to the connection formed when pin 31a joins wire 46, as shown in FIG. 10B. A ground connection is similarly made through pin 31b, and the battery in controller 102 is charged through pin 31c.

In this example, docking station 1300 performs two primary functions. The first function of docking station 1300 is to recharge the battery of controller 102. To do so, docking station 1300 is typically electrically coupled to a power source such as an electrical wall outlet. Docking station 1300 converts the power from the electrical wall outlet to an appropriate form and then provides the power to the power supply (e.g., 902 shown in FIG. 20) of controller 102.

The second function of docking station 1300 is to communicate data between controller 102 and a communication network. Controller 102 can send data to docking station 1300 and can receive data from docking station 1300. This function is described in more detail with reference to FIG. 25.

Some embodiments of docking station 1300 provide only one of these functions. Other embodiments provide additional features and functionality. For example, some embodiments of docking station 1300 allow multiple devices 100 to communicate with each other when connected with docking station 1300. In other examples, docking station 1300 is also configured to communicate with one or more computers accessible through a network, as described below. This allows for interactive data sharing between devices in order to promote, for example, greater efficiency in hospitals. Connection to the docking station 1300 allows nurses to keep a record of pain management for patients, and thereby increase the quality of care.

Docking station 1300 includes status indicators 1310 associated with each slot of docking station 1300. In this example, status indicators 1310 include a data communication indicator and a charging indicator. The data communication indicator is a light emitting diode (LED) that illuminates when the docking station 1300 is communicating with the respective controller 102. The charging indicator is an LED that illuminates when docking station 1300 is charging the respective controller 102. Other embodiments include additional status indicators 1310. Other types of status indicators include audible status indicators (e.g., speakers, buzzers, alarms, and the like) and visible status indicators (e.g., lights, liquid crystal displays, display screens, and the like).

Docking station 1300 is not limited to connection with a single type of controller 102. Multiple types of controllers 102 can be connected with docking station 1300 at any one time, if desired. For example, controllers 102 include a TENS device, an iontophoresis device, a muscle stimulation device (e.g., a neuromuscular electrical stimulation (NMES) device), a wound healing device, an interferential device, or other devices.

In some examples, docking station 1300 is configured to be used at a patient's home, such as in a bathroom or kitchen. Docking station 1300 can include multiple stations for charging different types of devices, as well as drawers and other conveniences that allow docking station 1300 to be used for multiple purposes.

Figure 25:
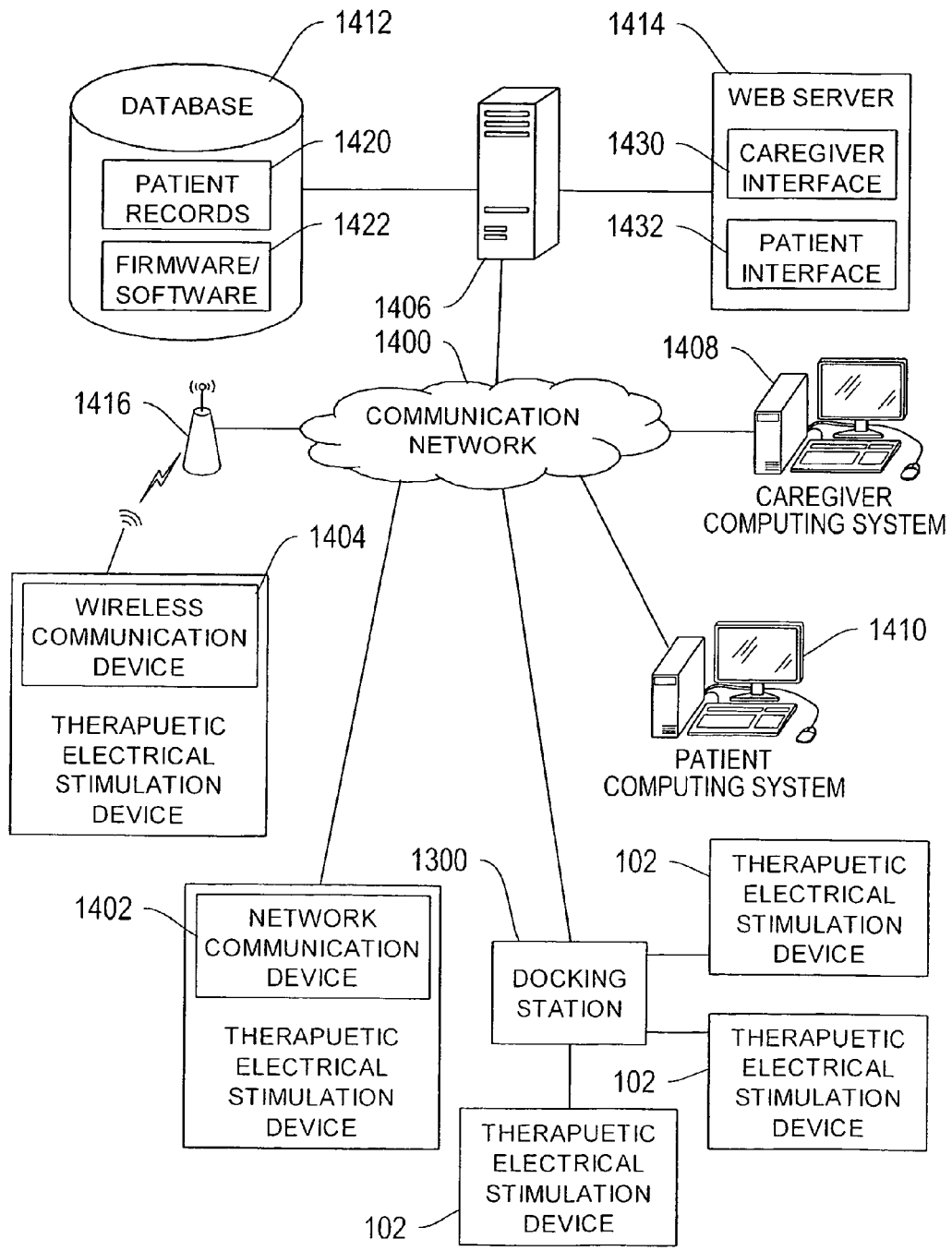
FIG. 25 is a block diagram of an exemplary system for communicating across a communication network including the device shown in FIG. 12.

FIG. 25 is a block diagram of an exemplary system for communicating across communication network 1400 involving therapeutic electrical stimulation devices. The system includes devices 102, 1402, and 1404. Devices 102 are in data communication with docking station 1300, such as shown in FIG. 24. Device 1402 includes a wireless communication device and device 1404 includes a wired network communication device. The system also includes server 1406, caregiver computing system 1408, and patient computing system 1410. Server 1406 includes database 1412 and Web server 1414. System also includes wireless router 1416.

Communication network 1400 is a data communication network that communicates data signals between devices. In this example, communication network 1400 is in data communication with docking station 1300, device 1402, device 1404, server 1406, caregiver computing system 1408, patient computing system 1410, and wireless router 1416. Docking station 1300 is in data communication with devices 102. Wireless router 1416 is in data communication with device 1404. Examples of communication network 1400 include the Internet, a local area network, an intranet, and other communication networks.

In some embodiments, devices 102, 1402, and 1404 store, in memory, data relating to therapy delivery or other operational characteristics of the respective devices. Communication network 1400 can be used to communicate that data to another device. For example, the data is transferred to patient computing system 1410 or to caregiver computing system 1408. Once the data has been transferred to the computing system, the data is stored for review and analysis by the patient or the caregiver. Communication network 1400 can also be used to communicate data from devices 102, 1402, and 1404 to server 1406. Server 1406 stores the data in patient record 1420.

In some embodiments, server 1406 includes Web server 1414. Web server 1414 includes caregiver interface 1430 patient interface 1432. Additional interfaces are provided in some embodiments to third parties, such as an insurance company. Web server 1414 generates web pages that are communicated across communication network 1400 using a standard communication protocol. An example of such a protocol is hypertext transfer protocol. The webpage data is arranged in a standard form, such as hypertext markup language. The webpage data is transferred across communication network 1400 and received by computing system 1408 and computing system 1410. A browser operating on respective computing system reads the webpage data and displays the webpage to the user.

Caregiver interface 1430 generates a webpage intended for use by a caregiver. The caregiver interface 1430 allows the caregiver to access patient records 1420 and generates reports or graphs to assist the caregiver in analyzing data from patient records 1420. In addition, caregiver interface 1430 provides technical or medical suggestions to the caregiver. In some embodiments, caregiver interface 1430 also allows the caregiver to request adjustments to an operational mode of a device 102, 1402, or 1404. The operational mode adjustments are then communicated from server 1406 to the device, and the device makes the appropriate mode adjustments.

Patient interface 1432 generates a webpage intended for use by a patient. In one example, patient interface 1432 allows the patient to access patient records 1420 and generates reports or graphs that assist the patient in analyzing data from patient records 1420. Patient interface 1432 provides instructions to assist the patient with uploading data from device 102, 1402, or 1404 to patient records 1420. Instructions or other educational information is also provided by patient interface 1432, if desired.

In some embodiments, database 1412 includes firmware repository 1422. Firmware repository 1422 includes data instructions that define the logical operation of a controller 102 (e.g. firmware 934 shown in FIG. 20). Firmware repository 1422 is used in some embodiments to store various versions of firmware. For example, when a new firmware version is created, the developer stores the new version of firmware in the firmware repository 1422. The firmware is then communicated to the appropriate devices 102, 1402, or 1404. The communication of new firmware versions can be either automatically distributed, or provided as an option to a patient or caregiver through interfaces 1430 and 1432. In some embodiments, patient interface 1432 requires that a patient agree to pay for an upgraded firmware version before the firmware is made available for installation on a device.

In another embodiment, firmware repository 1422 includes different firmware algorithms. Each firmware algorithm is specifically tailored to provide a specific therapy when executed by devices 102, 1402, 1404 or to be used with a particular hardware configuration. Examples of therapies defined by separate firmware algorithms include TENS, interferential therapy, edema therapy, muscle stimulation, iontophoresis therapy, and other therapies. A different firmware algorithm can also be specifically tailored for particular hardware configurations, such as for particular electrode numbers or configurations, for particular data communication devices, for different docking stations, or to accommodate other differences in hardware configuration.

For example, a patient may first obtain a TENS device including a patch shown in FIG. 12. The device includes a first firmware type that defines an algorithm appropriate for TENS therapy. Later, the patient desires to upgrade the device to cause the device to operate as an iontophoresis device. To do so, the patient uses patient computing system 1410 to access patient interface 1432. The patient selects a new firmware algorithm that is designed for iontophoresis therapy. The patient purchases and downloads the firmware associated with the iontophoresis therapy and loads the firmware onto the device. If necessary, an appropriate patch can be purchased through patient interface 1432 and delivered to the patient. The patch is then connected to the device controller and the new firmware algorithm is executed. The firmware causes the device to provide the desired iontophoresis therapy. In this way, some embodiments of controller 102 are customizable to provide multiple different therapies.

In another embodiment, firmware is specially tailored for providing a therapy to a particular part of the body. As a result, separate firmware algorithms are available for the treatment of separate body parts and conditions associated with those body parts. Such firmware algorithms can be obtained by downloaded, as described above.

In some embodiments, controllers 11, 100 include graphical user interfaces that allow the user to control the controllers 11, 100 and the therapy provided thereby. For example, the controllers can include built-in displays that are used to present the user interfaces. The user interfaces have home pages that allow the user to control various aspects of the controller, such as turning the device on and off, the type of therapy provided, and the intensity of the therapy.

In other examples, a separate device is used to control the controllers 11, 100. This device can communicate with the controllers 11, 100 through wired or wireless means (e.g., Wifi, Bluetooth). For example, a docking station (e.g., docking station 1300 described above) can include a user interface that is programmed to control the therapy provided by controllers 11, 100. The docking station can communicate wirelessly with controllers 11, 100.

In some examples, controllers 11, 100 can include additional functionality, such as open lead detection. If a lead looses contact with a surface that is being delivered therapy, controllers 11, 100 are programmed to detect the open lead and to modify therapy appropriately until the lead again makes contact. For example, controllers 11, 100 can be programmed to shut down therapy that is delivered to the open lead and to issue an alarm so that the user can replace the lead.

In other examples, controllers 11, 100 are programmed to sense feedback from the user and modify therapy accordingly. For example, controllers 11, 100 can be programmed to sense electromyographic biofeedback based on muscle activity and regulate therapy accordingly. In other examples, controllers 11, 100 are programmed to sense impedance and deliver therapy accordingly. In other examples, other biofeedback such as heart rate or activity levels can also be monitored. Other configurations are possible.

In some examples, the user can provide specific feedback as well. For example, the user can set pain thresholds that controllers 11, 100 are programmed to remember. In other examples, the pain thresholds can be set automatically by controllers 11, 100 by monitoring capacitance levels.

In yet other examples, controllers 11, 100 can include accelerometers and/or gyroscopes that can be used to measure orientation and activity level of the patient. For example, therapy can be adjusted based on the orientation of the patient (e.g., lying down or upright), as well as activity level. Controllers 11, 100 can be programmed to adjust therapy over a specific time. In yet other examples, multiple controllers can be used, and the controllers can be programmed to communicate with each other to synchronize the therapy that is delivered to the user, thereby forming a body area network. This network can be formed through wireless communication and/or conductive communication through the patient's body.

The number of delivery channels can be modified (e.g., 2 channel vs. 4 channel) to modify the type and intensity of therapy. Also, devices can be connected in series to deliver an increase in therapy intensity or increase the area treated.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the disclosure.

What is claimed is:

1. A system for delivering therapeutic electrical stimulation, comprising:
   a garment;
   at least one shoe attached to the garment, the at least one shoe being configured to couple to at least one controller;
   a plurality of electrodes connected to the garment, wherein the electrodes are positioned adjacent the garment; and
   at least one lead wire electrically connecting the plurality of electrodes to the at least one shoe.

2. The system of claim 1, wherein the garment comprises at least two layers and the shoe comprises a base, and wherein the base is positioned between the at least two layers of the garment for physically holding the shoe within the garment.

3. The system of claim 2, wherein the at least one lead wire is positioned between the at least two layers of the garment.

4. The system of claim 2, wherein the shoe is exposed on an outer side of the garment to allow connection to the at least one controller.

5. The system of claim 1, wherein the garment comprises a belt configured to be worn around certain anatomy of a patient.

6. The system of claim 1, wherein the shoe is attached to the garment by at least one of: stitching, gluing or embedding in a laminate layer.

7. The system of claim 1, wherein the plurality of electrodes are positioned on the garment in a grid pattern.

8. The system of claim 1, wherein the plurality of electrodes are connected to the garment by at least one of: sewing, gluing, or velcroing.

9. The system of claim 1, further comprising at least one electrically conductive snap connected to the garment for mechanically and electrically securing the plurality of electrodes to the garment.

10. The system of claim 9, wherein the at least one snap is connected to the at least one lead wire.

11. The system of claim 1, wherein the shoe is configured to be removably mechanically connected to the at least one controller at a receptacle, and wherein the shoe is configured to be electrically coupled to the at least one lead wire at the receptacle.

12. The system of claim 11, wherein the electrodes are configured to be connected to the shoe and the controller via the at least one lead wire, wherein the at least one lead wire is configured to extend from the shoe and to connect to an electrical connector.

13. The system of claim 12, comprising a first electrode, a second electrode, a first lead wire and a second lead wire, wherein the first lead wire connects to the shoe through the electrical connector and a signal pin in the receptacle, and wherein the second lead wire connects to the shoe through electrical connector to a ground pin in the receptacle, such that in use, a voltage potential is generated between the first electrode and the second electrode, a current enters skin of a wearer of the garment through the first electrode, the current passes through the skin, and then the current returns from the skin through the second electrode.

14. The system of claim 12, wherein the shoe comprises a first portion that defines a channel sized to receive a railway platform of the controller when the first portion of the shoe is inserted into a controller receptacle.

15. The system of claim 14, wherein the railway platform is configured to slide inside the channel below the first portion of the shoe and above a bottom surface defining the channel, thereby fitting in a 'U' shape around a second portion of the shoe.

16. The system of claim 15, wherein the first portion comprises a clip member sized to engage a detent or a lip of a member of the controller when the first portion of the shoe is fully inserted into the controller receptacle to retain the first portion of the shoe within the receptacle.

17. The system of claim 16, wherein the clip member is configured to engage the detent or the lip of the member of controller such that upon engagement an affirmative "click" sound is generated indicating that the shoe is connected to the controller.

18. The system of claim 14, wherein a base of the shoe comprises two side flanges configured to slide under and at least partially abut respective side portions of the controller.

19. The system of claim 14, comprising a plurality of receptacles on a front face of the first portion of the shoe, wherein each receptacle is housed inside of the first portion of the shoe, wherein the plurality of receptacles is configured to provide an electrical signal, a connection to ground, and a battery charging connection.

20. The system of claim 19, wherein each of the plurality of receptacles is sized to receive pins of the controller when the front portion of the shoe is fully inserted into a connector receptacle.

21. The system of claim 20, wherein the pins extend generally parallel to the railway platform.

22. The system of claim 12, wherein the shoe includes two symmetric halves configured for insertion of the electrical connector inside the shoe.

23. The system of claim 12, wherein the electrical connector is in line with a path of entry of the shoe into the receptacle.

24. The system of claim 12, wherein the electrical connector directly surrounds a point of entry of the shoe into the receptacle.

25. The system of claim 12, wherein the electrical connector of the shoe is configured to mate with electrical connectors of electrical circuitry, wherein the electrical circuitry is configured to program the controller.

* * * * *

UNITED STATES PATENT AND TRADEMARK OFFICE
CERTIFICATE OF CORRECTION

PATENT NO.        : 8,768,473 B2                                        Page 1 of 1
APPLICATION NO.   : 13/868587
DATED             : July 1, 2014
INVENTOR(S)       : Bachinski et al.

It is certified that error appears in the above-identified patent and that said Letters Patent is hereby corrected as shown below:

In the Specification

Column 15 at line 16, Change "1020N" to --102 ON--.

Column 15 at line 54, Change "1020N" to --102 ON--.

Column 16 at line 47, Change "1020N" to --102 ON--.

Signed and Sealed this
Third Day of February, 2015

Michelle K. Lee
*Deputy Director of the United States Patent and Trademark Office*